United States Patent
McDevitt et al.

(10) Patent No.: US 12,343,407 B2
(45) Date of Patent: Jul. 1, 2025

(54) INFLAMMASOME-TARGETED RNA INTERFERENCE APPROACH TO TREATING KIDNEY INJURY AND DISEASE

(71) Applicant: MEMORIAL SLOAN KETTERING CANCER CENTER, New York, NY (US)

(72) Inventors: Michael R. McDevitt, New York, NY (US); David A. Scheinberg, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 862 days.

(21) Appl. No.: 17/434,317

(22) PCT Filed: Feb. 26, 2020

(86) PCT No.: PCT/US2020/019987
§ 371 (c)(1),
(2) Date: Aug. 26, 2021

(87) PCT Pub. No.: WO2020/176679
PCT Pub. Date: Sep. 3, 2020

(65) Prior Publication Data
US 2022/0168444 A1   Jun. 2, 2022

Related U.S. Application Data

(60) Provisional application No. 62/811,498, filed on Feb. 27, 2019.

(51) Int. Cl.
| | | |
|---|---|---|
| A61K 47/69 | (2017.01) | |
| A61K 31/713 | (2006.01) | |
| A61K 45/06 | (2006.01) | |
| A61P 13/12 | (2006.01) | |
| G01N 33/68 | (2006.01) | |
| C12Q 1/68 | (2018.01) | |

(52) U.S. Cl.
CPC ........ *A61K 47/6923* (2017.08); *A61K 31/713* (2013.01); *A61K 45/06* (2013.01); *A61K 47/6929* (2017.08); *A61P 13/12* (2018.01); *G01N 33/6893* (2013.01); *G01N 2333/705* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,858,648 B2 | 12/2010 | Bianco et al. |
| 8,540,965 B2 | 9/2013 | Scheinberg et al. |
| 9,629,927 B2 | 4/2017 | Scheinberg et al. |
| 2017/0145412 A1 | 5/2017 | Jiang et al. |
| 2017/0348234 A1 | 12/2017 | McDevitt et al. |
| 2019/0388454 A1* | 12/2019 | Karin ................ C12N 15/1137 |

FOREIGN PATENT DOCUMENTS

WO   WO-2016/014808 A1   1/2016

OTHER PUBLICATIONS

International Search Report on PCT PCT/US2020/019987 dtd Jul. 29, 2020.
Singh, et al., "Polyamine functionalized carbon nanotubes: synthesis, characterization, cytotoxicity and siRNA binding," Journal of Materials Chemistry, 2011, pp. 4850-4860, vol. 21.

* cited by examiner

*Primary Examiner* — Sean McGarry
(74) *Attorney, Agent, or Firm* — Foley & Lardner LLP

(57) ABSTRACT

The present disclosure relates generally to methods for treating, preventing, and/or ameliorating chronic kidney disease (CKD) and/or renal injury in a subject in need thereof. In particular, the methods disclosed herein comprise administering a therapeutically effective amount of a pharmaceutical composition comprising at least one Nlrp3 siRNA non-covalently conjugated to sidewall ammonium-functionalized carbon nanotubes (fCNTs), wherein the at least one Nlrp3 siRNA reduces the expression of NLR pyrin domain-containing protein 3 (NLRP3) in a subject diagnosed with, or at risk for CKD and/or renal injury.

25 Claims, 37 Drawing Sheets
Specification includes a Sequence Listing.

Vehicle - PBS (d14)

Folic acid only (d14)

Folic acid + 1x si*Nlrp3* (d7)

Folic acid + 2x si*Nlrp3* (d14)

si*Nlrp3* only (d14)

Vehicle - PBS (d14)

Folic acid only (d14)

Folic acid + 1x si*Nlrp3* (d7)

Folic acid + 2x si*Nlrp3* (d14)

si*Nlrp3* only (d14)

Vehicle - PBS (d14)

Folic acid only (d14)

Folic acid + 1x si*Nlrp3* (d7)

Folic acid + 2x si*Nlrp3* (d14)

siNlrp3 only (d14)

Vehicle - PBS (d14)

Folic acid only (d14)

Folic acid + 1x si*Nlrp3* (d7)

Folic acid + 2x si*Nlrp3* (d14)

siN*Nlrp3* only (d14)

Vehicle - PBS (d14)

Folic acid only (d14)

Folic acid + 1x si*Nlrp3* (d7)

Folic acid + 2x si*Nlrp3* (d14)

si*Nlrp3* only (d14)

Vehicle - PBS (d14)

Folic acid only (d14)

Folic acid + 1x si*Nlrp3* (d7)

Folic acid + 2x si*Nlrp3* (d14)

si*Nlrp3* only (d14)

Vehicle - PBS (d14)

Folic acid only (d14)

Folic acid + 1x si*Nlrp3* (d7)

Folic acid + 2x si*Nlrp3* (d14)

si*Nlrp3* only (d14)

INFLAMMASOME-TARGETED RNA INTERFERENCE APPROACH TO TREATING KIDNEY INJURY AND DISEASE

CROSS-REFERENCE TO RELATED APPLICATIONS

This application is a U.S. National Phase Application under 35 U.S.C. § 371 of International Application No. PCT/US2020/019987, filed Feb. 26, 2020, which claims the benefit of and priority to U.S. Provisional Appl. No. 62/811,498, filed Feb. 27, 2019, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Mar. 25, 2020, is named 115872-0598 SL.txt and is 5,715 bytes in size.

TECHNICAL FIELD

The present technology relates generally to methods for treating, preventing, and/or ameliorating chronic kidney disease and/or renal injury in a subject in need thereof. Also disclosed herein are methods for reducing the expression of NLR pyrin domain-containing protein 3 (NLRP3) to treat, prevent, and/or ameliorate chronic kidney disease.

STATEMENT OF U.S. GOVERNMENT SUPPORT

This invention was made without direct government support.

BACKGROUND

The following description of the background of the present technology is provided simply as an aid in understanding the present technology and is not admitted to describe or constitute prior art to the present technology.

Chronic kidney disease (CDK), also known as chronic renal failure (CRF), is a serious medical condition of the kidneys and a worldwide public health problem. CKD is characterized by a substantive decline in glomerular filtration rate (GFR), decreased urine output, or both. Other complications of CKD include high blood pressure, anemia (low blood count), weak bones, poor nutritional health, and nerve damage. CKD is the ninth leading cause of death in the United States, and global CKD prevalence is estimated to 11-13%. Subjects with CKD generally experience progressive loss of kidney function and are at risk for end-stage renal disease (ESRD). The prevalence of ESRD is 3.7 times greater in African Americans, 1.4 times greater in Native Americans, and 1.5 times greater in Asian Americans. To date, there are no effective therapies for CKD.

SUMMARY OF THE PRESENT TECHNOLOGY

In one aspect, the present disclosure provides a pharmaceutical composition comprising a sidewall ammonium-functionalized carbon nanotube (fCNT) and an effective amount of at least one Nlrp3 siRNA that inhibits NLR pyrin domain-containing protein 3 (NLRP3) expression levels or activity in a cell, wherein the fCNT is non-covalently conjugated to the at least one Nlrp3 siRNA.

Additionally or alternatively, in some embodiments of the methods of the present technology, the subject displays elevated expression levels of NLRP3 protein in kidney cells prior to treatment. In certain embodiments, treatment with an effective amount of the pharmaceutical composition results in a decrease in NLRP3 and/or KIM1 expression levels in the subject compared to that observed in the subject prior to treatment.

In some embodiments of the methods of the present technology, the subject has been diagnosed as having acute kidney injury or CKD. The subject may exhibit signs or symptoms of CKD. Signs or symptoms of CKD may include one or more of metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis.

Additionally or alternatively, in some embodiments of the methods of the present technology, the pharmaceutical composition is administered orally, topically, intranasally, systemically, intravenously, subcutaneously, intraperitoneally, intradermally, intraocularly, iontophoretically, transmucosally, or intramuscularly. In some embodiments, the pharmaceutical composition is administered daily for 6 weeks or more. In other embodiments, the pharmaceutical composition is administered daily for 12 weeks or more.

Additionally or alternatively, in some embodiments, the methods further comprise separately, sequentially or simultaneously administering one or more additional therapeutic agents to the subject. Examples of the one or more additional therapeutic agents include benazepril, captopril, enalapril, ramipril, lisinopril, azilsartan, candesartan, eprosartan, irbesartan, losartan, olmesartan, telmisartan, valsartan, atenolol, carvedilol, metoprolol, propranolol, amlodipine, diltiazem, felodipine, isradipine, nicardipine, nifedipine, nisoldipine, verapamil, pepstatin, CGP2928, aliskiren, chlorthalidone, chlorthiazide, hydrochlorthiazide, indapamide, metolazone, amiloride, bumetanide, furosemide, spironolactone, triamterene, or combinations thereof.

In another aspect, the present disclosure provides a method for inhibiting kidney cell fibrosis and inflammation in a subject in need thereof, comprising administering to the subject a therapeutically effective amount of the pharmaceutical composition.

Also described herein are methods for monitoring the therapeutic efficacy of the pharmaceutical composition in a subject diagnosed with CKD comprising: (a) detecting NLRP3 protein levels in a test sample obtained from the subject after administration of the pharmaceutical composition of the present technology; and (b) determining that the pharmaceutical composition is therapeutically effective when the NLRP3 protein levels in the test sample of step (a) are reduced compared to that observed in a control sample obtained from the subject prior to administration of the pharmaceutical composition.

Also provided herein are kits comprising one or more pharmaceutical compositions comprising at least one siNlrp3/fCNTs disclosed herein and instructions for use.

BRIEF DESCRIPTION OF THE DRAWINGS

FIG. 2(A) shows blood chemistry levels of BUN (mg/dL) for naïve mice, mice treated only with FA, and FA-injured mice treated with prophylactic siNlrp3/fCNT. FIG. 2(B) shows blood chemistry levels of serum creatinine (mg/dL) for naïve mice, mice treated only with FA, and FA-injured mice treated with prophylactic siNlrp3/fCNT. FIG. 2(C) shows blood chemistry levels of phosphorous (mg/dL) for naïve mice, mice treated only with FA, and FA-injured mice treated with prophylactic siNlrp3/fCNT. FIG. 2(D) shows blood chemistry levels of magnesium (mg/dL) for naïve mice, mice treated only with FA, and FA-injured mice treated with prophylactic siNlrp3/fCNT.

FIG. 3(A) provides the H&E staining of a kidney samples from the vehicle group (mice administered PBS only, sacrificed on day 14); FIG. 3(B) provides the H&E staining of a kidney samples from the folic Acid only group (mice administered single dose of folic acid, sacrificed on day 14); FIG. 3(C) provides the H&E staining of a kidney samples from the folic Acid+1× siNlrp3/fCNT group (mice administered single dose of folic acid with a single dose of siNlrp3/fCNT 48 hours later, sacrificed on day 7); FIG. 3(D) provides the H&E staining of a kidney samples from the folic Acid+2× siNlrp3/fCNT group (mice administered single dose of folic acid following with two doses of siNlrp3/fCNT 48 hours and 7 days later, sacrificed on day 14), and FIG. 3(E) provides the H&E staining of a kidney samples from the siNlrp3-only group (mice administered siNlrp3, sacrificed on day 14). FIG. 3(F) provides the results where H&E stained tissue morphology was examined to assess changes after treatment for each mouse (scale bar=100 μm), where all H&E sections were blindly scored using a semi-quantitative scale from 0 to 4 (0=no lesions; 1=minimal lesions; 2=mild lesions; 3=moderate lesions; and 4=marked lesions). Data are individual animals with means±SEM (n=3).

FIG. 4(A) provides images (after staining with picrosirius red) of the vehicle group (mice administered PBS only, sacrificed on day 14); FIG. 4(B) provides images (after staining with picrosirius red) of the Folic Acid only group (mice administered single dose of folic acid, sacrificed on day 14), FIG. 4(C) provides images (after staining with picrosirius red) of the Folic Acid+1× siNlrp3/fCNT group (mice administered single dose of folic acid with a single dose of siNlrp3/fCNT 48 hours later, sacrificed on day 7), FIG. 4(D) provides images (after staining with picrosirius red) of the Folic Acid+2× siNlrp3/fCNT group (mice administered single dose of folic acid following with two doses of siNlrp3/fCNT 48 hours and 7 days later, sacrificed on day 14), and FIG. 4(E) provides images (after staining with picrosirius red) of the siNlrp3 only group (mice administered siNlrp3, sacrificed on day 14). Significant collagen type I and III fibril deposits were evident within the interstitial fibrotic lesions in the Folic Acid only group (indicated by the arrow); no significant fibrosis was present in remaining groups (scale bars=50 μm, n=3).

FIG. 5(A) provides representative images of the Vehicle group (mice administered PBS only, sacrificed on day 14), FIG. 5(B) provides representative images of the Folic Acid only group (mice administered single dose of folic acid, sacrificed on day 14), FIG. 5(C) provides representative images of the Folic Acid+1× siNlrp3/fCNT group (mice administered single dose of folic acid with a single dose of siNlrp3/fCNT 48 hours later, sacrificed on day 7), FIG. 5(D) provides representative images of the Folic Acid+2× siNlrp3/fCNT group (mice administered single dose of folic acid following with two doses of siNlrp3/fCNT 48 hours and 7 days later, sacrificed on day 14), FIG. 5(E) provides representative images of the siNlrp3 only group (mice administered siNlrp3, sacrificed on day 14). Significant collagen deposits were evident within the interstitial fibrotic lesions in the Folic Acid only group (indicated by arrow); no significant fibrosis was present in remaining groups (scale bars=200 μm, n=3).

FIG. 6(A) provides representative images from the Vehicle group (mice administered PBS only, sacrificed on day 14), FIG. 6(B) provides representative images from the Folic Acid only group (mice administered single dose of folic acid, sacrificed on day 14), FIG. 6(C) provides representative images from the Folic Acid+1× siNlrp3/fCNT group (mice administered single dose of folic acid with a single dose of siNlrp3/fCNT 48 hours later, sacrificed on day 7), FIG. 6(D) provides representative images from the Folic Acid+2× siNlrp3/fCNT group (mice administered single dose of folic acid following with two doses of siNlrp3/fCNT 48 hours and 7 days later, sacrificed on day 14), FIG. 6(E) provides representative images from the siNlrp3 only group (mice administered siNlrp3, sacrificed on day 14). Significant mucopolysaccharide deposits were evident within the interstitial fibrotic lesions in the Folic Acid only group stained (indicated by arrows); staining in remaining groups was less intense (scale bars=50 μm, n=3).

FIG. 7(A) provides representative images from the Vehicle group (mice administered PBS only, sacrificed on day 14), FIG. 7(B) provides representative images from the Folic Acid only group (mice administered single dose of folic acid, sacrificed on day 14), FIG. 7(C) provides representative images from the Folic Acid+1× siNlrp3/fCNT group (mice administered single dose of folic acid with a single dose of siNlrp3/fCNT 48 hours later, sacrificed on day 7), FIG. 7(D) provides representative images from the Folic Acid+2× siNlrp3/fCNT group (mice administered single dose of folic acid following with two doses of siNlrp3/fCNT 48 hours and 7 days later, sacrificed on day 14), and FIG. 7(E) provides representative images from the siNlrp3 only group (mice administered siNlrp3, sacrificed on day 14). An increase in CD3 positive cell populations was observed in the Folic Acid only group; no significant increase was present in remaining groups (scale bars=50 μm, n=3).

FIG. 8(A) provides representative images from the Vehicle group (mice administered PBS only, sacrificed on day 14), FIG. 8(B) provides representative images from the Folic Acid only group (mice administered single dose of folic acid, sacrificed on day 14), FIG. 8(C) provides representative images from the Folic Acid+1× siNlrp3/fCNT group (mice administered single dose of folic acid with a single dose of siNlrp3/fCNT 48 hours later, sacrificed on day 7), FIG. 8(D) provides representative images from the Folic Acid+2× siNlrp3/fCNT group (mice administered single dose of folic acid following with two doses of siNlrp3/fCNT 48 hours and 7 days later, sacrificed on day 14), and FIG. 8(E) provides representative images from the siNlrp3 only group (mice administered siNlrp3, sacrificed on day 14). An increase in PD-1 positive cell populations was observed in the Folic Acid only group; no significant increase was present in remaining groups (scale bars=50 µm, n=3).

FIG. 9(A) provides representative images from the Vehicle group (mice administered PBS only, sacrificed on day 14), FIG. 9(B) provides representative images from the Folic Acid only group (mice administered single dose of folic acid, sacrificed on day 14), FIG. 9(C) provides representative images from the Folic Acid+1× siNlrp3/fCNT group (mice administered single dose of folic acid with a single dose of siNlrp3/fCNT 48 hours later, sacrificed on day 7), FIG. 9(D) provides representative images from the Folic Acid+2× siNlrp3/fCNT group (mice administered single dose of folic acid following with two doses of siNlrp3/fCNT 48 hours and 7 days later, sacrificed on day 14), FIG. 9(E) provides representative images from the siNlrp3 only group (mice administered siNlrp3, sacrificed on day 14). An increase in Iba1 positive cell populations was observed in the Folic Acid only group; no significant increase was present in remaining groups (scale bars=50 µm, n=3).

DETAILED DESCRIPTION

Figure 1:
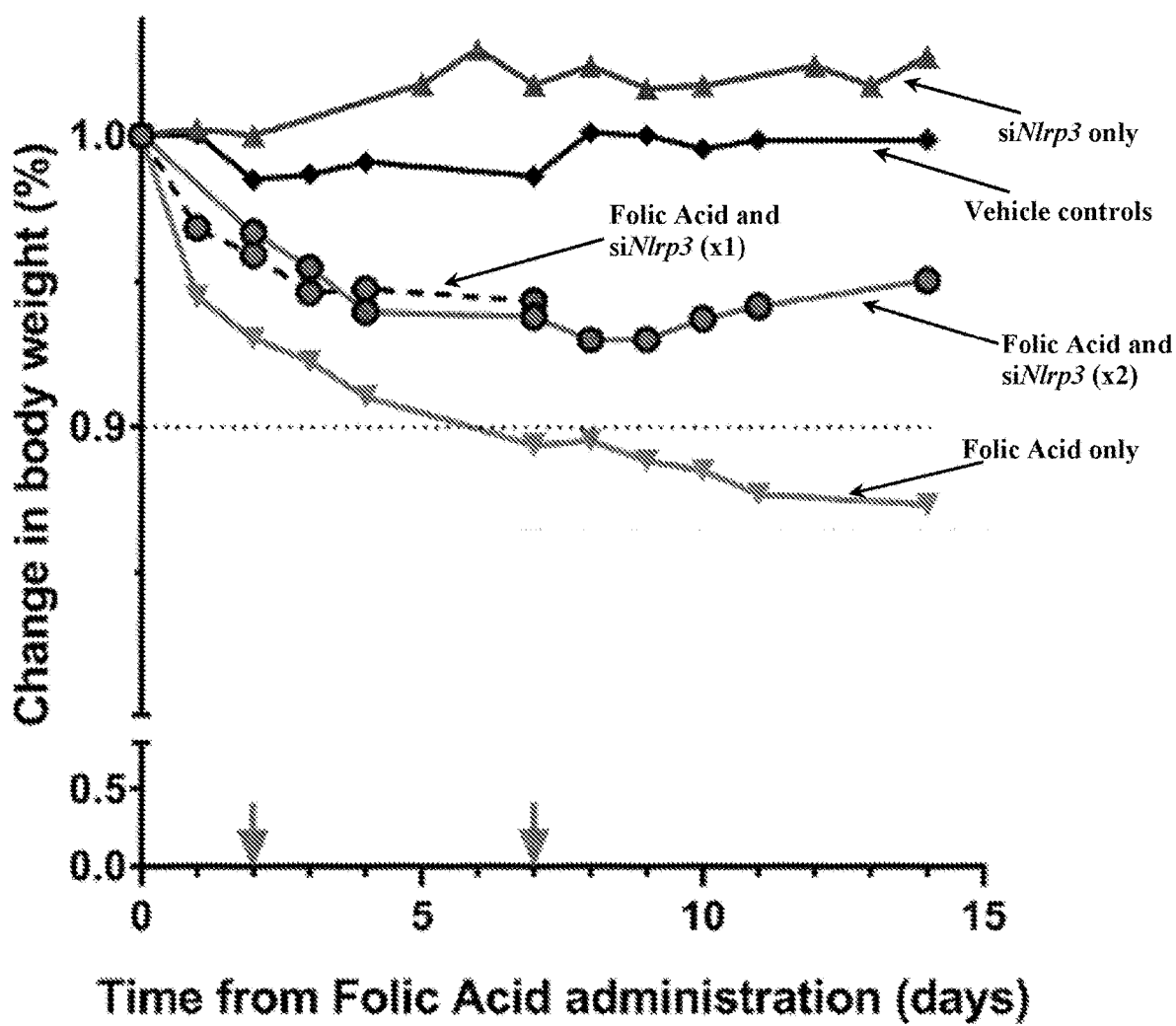
FIG. 1 demonstrates that siNlrp3/fCNT intervention is bio-compatible and non-toxic to mice. siNlrp3/fCNT was delivered to the renal proximal tubule cells 2 and 7 days after folic acid (FA) injury. Treatment schedule indicated with downward arrows on the X-axis. Control groups included siNlrp3 only to examine the biocompatibility of siNlrp3 in the absence of FA; naïve animals receiving only vehicle (i.e., no RNA interference or FA); and FA only injury with no treatment.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual;* Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization;* Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 weight %" would be understood to mean "9 weight % to 11 weight %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complementary sequence can also be an RNA sequence complementary to the DNA sequence or its complementary sequence, and can also be a cDNA.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of renal injury and/or chronic kidney disease (CKD). Signs or symptoms of CKD may include one or more of metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE;

Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. The exact size of the oligonucleotide will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, "prevention", "prevent", or "preventing" of a disorder or condition refers to one or more compounds that, in a statistical sample, reduces the occurrence or progression of the disorder or condition in the treated sample relative to an untreated control sample, or delays the onset of one or more symptoms of the disorder or condition relative to the untreated control sample. As used herein, preventing CKD, includes preventing or delaying the initiation of symptoms of CKD. As used herein, prevention of CKD also includes preventing a recurrence of one or more signs or symptoms of CKD. Signs or symptoms of CKD may include one or more of metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis.

As used herein, the term "sample" refers to clinical samples obtained from a subject. Biological samples may include tissues, cells, protein or membrane extracts of cells, mucus, sputum, bone marrow, bronchial alveolar lavage (BAL), bronchial wash (BW), and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

The term "specific" as used herein in reference to an oligonucleotide means that the nucleotide sequence of the oligonucleotide has at least 12 bases of sequence identity with a portion of a target nucleic acid when the oligonucleotide and the target nucleic acid are aligned. An oligonucleotide that is specific for a target nucleic acid is one that, under the stringent hybridization or washing conditions, is capable of hybridizing to the target nucleic acid of interest and not substantially hybridizing to nucleic acids which are not of interest. Higher levels of sequence identity are desirable and include at least 75%, at least 80%, at least 85%, at least 90%, at least 95% or at least 98% sequence identity.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "subject," "individual," or "patient" are used interchangeably and refer to an individual organism, a vertebrate, a mammal, or a human. In certain embodiments, the individual, patient or subject is a human.

As used herein, the terms "target sequence" and "target nucleic acid sequence" refer to a specific nucleic acid sequence to be modulated (e.g., inhibited or downregulated). In some embodiments, the target nucleic acid sequence is NLRP3.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

Functionalized Carbon Nanotubes of the Present Technology

Carbon nanotubes (CNTs) are allotropes of carbon with a cylindrical nanostructure. The carbon atoms are all surface atoms formed in regular structures with defined periodicity. The CNTs may be fibrillar (i.e., have an aspect (length-to-diameter) ratio greater than 1), and in any embodiment herein the CNTs may have an aspect ratio from 1.1 to about $10^5$ (such as from about 11 to about $10^5$). The CNTs may be single-walled CNTs (SWCNTs), multi-walled carbon nanotubes (MWCNTs), or a mixture of both.

The CNTs of the present application are functionalized carbon nanotubes (fCNTs) that include direct covalent sidewall functionalization of the CNT to provide primary ammonium ($—NH_3^+$) groups or primary ammonium-bearing moieties. Hereinafter, such direct covalent sidewall functionalization of the CNT to provide primary ammonium groups or primary ammonium-bearing moieties may be referred to as "sidewall ammonium functionalized" in the present disclosure and in the claims. Direct covalent sidewall functionalization is associated with a change in hybridization of the effected carbons in the CNT sidewall from $sp^2$ (in the original CNT sidewall) to $sp^3$ upon functionalization. Indirect covalent functionalization is associated with chemical transformations of carboxylic groups at the open ends and holes in the sidewalls. In any embodiment herein, the fCNTs may further include indirect covalent functionalization.

In any embodiment herein, the primary ammonium-bearing moieties may include moities represented by Formula I

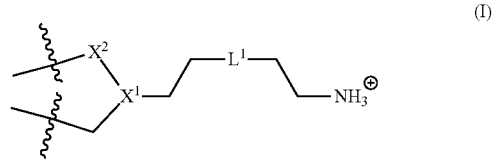

wherein $X^1$ is O, NH, or $CH_2$; $X^2$ is N or CH; and $L^1$ is an alkylene glycol (such as a propylene glycol or ethylene glycol), a polyalkylene glycol (such as a poly(propylene glycol) or poly(ethylene glycol)), $—NHC(O)CH(CO_2H)—$, or carbon, hydrogen, oxygen, nitrogen, sulfur, or other atom composed chain, or a combination of any two or more thereof. In any embodiment herein, the moiety of Formula I may be a moiety of Formula Ia:

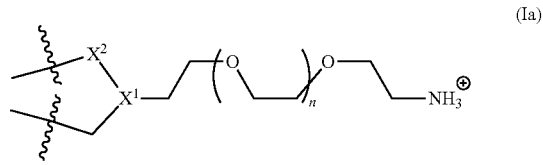

wherein n is 1, 2, 3, 4, 5, 6, 7, 8, 9, 10, or 11-100.

In any embodiment herein, the fCNTs may have an average length of about 10-100,000 nm, about 30-1000 nm, about 30-300 nm, about 30-100 nm, about 100-3000 nm, about 100-1000 nm, about 100-300 nm, about 300-3000 nmm, or about 300-1000 nm. In any embodiment herein, the fCNTs may have an average length of about 100-600 nm, about 100-500 nm, about 100-400 nm, about 200-600 nm, about 200-500 nm, about 200-400 nm or about 250-350 nm. In any embodiment herein, the fCNTs may have an average length of about 300 nm. Length can be determined by transmission electron or atomic force microscopy, dynamic light scater or any appropriate physicochemical method including chromatography.

In any embodiment herein, the fCNTs may have an average diameter of about 0.1-100 nm, about 0.1-10 nm, about 0.1-3 nm, about 0.1-1 nm, about 0.1-0.3 nm, about 0.3-30 nm, about 0.3-10 nm, about 0.3-3 nm, about 0.3-1 nm, about 1-30 nm, about 1-10 nm, about 1-3 nm, about 3-30 nm, about 3-10 nm, or about 10-30 nm. In any embodiment herein, the fCNTs may an average diameter of about 0.5-1.5 nm, about 0.6-1.4 nm, about 0.7-1.3 nm, about 0.8-1.2 nm or about 0.9-1.1 nm. In any embodiment herein, the fCNTs may have an average diameter of about 1 nm. Diameter can be determined by transmission electron or atomic force microscopy, dynamic light scater or any appropriate physicochemical method including Raman spectroscopy or chromatography.

Nlrp3 siRNAs of the Present Technology

In one aspect, the present disclosure provides pharmaceutical compositions comprising fCNTs that are non-covalently conjugated to at least one Nlrp3 siRNA ("siNlrp3/fCNT complex" or "siNlrp3/fCNTs"). Non-covalent conjugation is associated with supramolecular complexation via various adsorption bonding forces, such as Van der Waals force, hydrogen bonds, electrostatic forces, it-stacking interactions, or a combination of any two or more thereof. Thus, the average molar ratio of Nlrp3 siRNA non-covalently conjugated to the fCNTs in the siNlrp3/fCNT complex may be about 1, about 2, about 3, about 4, about 5, or any range including and/or in between any two of these values, and/or up to 10 to 100. Such a number-weighted average molar ratio may be generated via mixing the fCNTs and Nlrp3 siRNA together at the desired ratio at ambient temperature. Spectrophotometric titration methods described in Alidori et al (J Phys Chem) can be used to measure loading stoichiometry as well as NMR, mass spectroscopy or chromatography.

The at least one Nlrp3 siRNA may comprise a sense strand (s) and an antisense strand (as), wherein the antisense strand comprises a 20-27 base pair nucleic acid sequence that is complementary to a portion of a NLRP3 nucleic acid sequence selected from the group consisting of SEQ ID NO: 1 and SEQ ID NO: 2. Shorter (<20) and longer (>27) base pair sequences are also applicable as sense and anti-sense strands. SEQ ID NO: 1 corresponds to exon 4 of murine NLRP3. SEQ ID NO: 2 corresponds to exon 3 of human NLRP3.

```
Exon 4 of murine NLRP3 (SEQ ID NO: 1):
att actgtaagat gtacagacga catgtgagaa gcaggttcta ctctatcaag gacaggaacg cgcgtctagg tgagagtgtg gacctcaaca gtcgctacac gcagctccaa ctggtcaagg agcatccaag caagcaggag cgggagcatg aactcctgac catcggccgg actaaaatgc gggacagccc catgagttcc cttaagctgg agctgctgtt tgagcccgag gacgggcact cggagcctgt gcacacagtg gtgttccagg gagcagcagg catcgggaaa accatcctag ccaggaagat tatgttggac tgggcactgg gaaagctctt caaagacaaa tttgactatt tgttctttat ccactgccga gaggtgagcc tcaggacgcc aaggagtcta gcagacctga ttgtcagctg ctggcctgac ccaaacccac cagtgtgcaa gatcctgcgc aagccttcca ggatcctctt cctcatggat ggctttgatg agctacaagg ggcctttgac gagcacattg gggaggtctg cacagactgg caaaaggctg tgcggggaga cattctgcta agcagcctca tccgaaagaa actgctgccc aaggcctctc tgctcataac gacgaggccg gtagccttgg agaaactgca gcatctcctg gaccacccc gccatgtgga gatcctaggt ttctctgagg ccaaaaggaa ggagtatttc tttaagtatt tctccaacga gctgcaggcc cgggaggcct tcaggctgat ccaagagaat gaggtcctct ttaccatgtg cttcatcccc ctggtctgct ggattgtgtg cacggggcta aagcaacaga tggagaccgg gaagagcctg gcccagacct ccaagaccac tacggccgtc tacgtcttct tcctttccag cctgctgcaa tcccgggggg gcattgagga gcatctcttc tctgactacc tacagggct ctgttcactg gctgcggatg gaatttggaa ccagaaaatc ctatttgagg agtgtgatct gcggaagcac ggcctgcaga agactgacgt ctccgctttc ctgaggatga acgtgttcca gaaggaagtg gactgcgaga gattctacag cttcagccac atgactttcc aggagttctt cgctgctatg tactatttgc tggaagagga ggcagagggg gagaccgtga ggaaaggacc aggaggttgt tcagatcttc tgaaccgaga cgtgaaggtc ctactagaaa attacggcaa gtttgaaaaa ggctatctga tttttgttgt ccgattcctc tttggccttg taaaccagga gagaacctct tatttggaga agaaactaag ttgcaagatc tctcagcaag tcagactgga actactgaag tggattgaag tgaaagccaa ggccaagaag ctgcagtggc agcccagcca actggaactg ttctactgcc tgtacgagat gcaggaggaa gactttgtgc agagtgccat ggaccacttt cccaaaattg agatcaacct ctctaccaga atggaccacg tggtttcctc cttttgtatt aagaactgtc atagggtcaa aacgctttcc ctgggttttt ttcacaactc gcccaaggag gaagaagaag agaggagagg aggtcgaccc ttggaccagg ttcagtgtgt
```

```
tttcccagac actcatgttg cctgttcttc cag
```

Exon 3 of human NLRP3 (SEQ ID NO: 2):
```
a ttaccgtaag aagtacagaa agtacgtgag aagcagattc cagtgcattg aagacaggaa tgcccgtctg ggtgagagtg tgagcctcaa caaacgctac acacgactgc gtctcatcaa ggagcaccgg agccagcagg agagggagca ggagcttctg gccatcggca agaccaagac gtgtgagagc cccgtgagtc ccattaagat ggagttgctg tttgaccccg atgatgagca ttctgagcct gtgcacaccg tggtgttcca gggggcggca gggattggga aaacaatcct ggccaggaag atgatgttgg actgggcgtc ggggacactc taccaagaca ggtttgacta tctgttctat atccactgtc gggaggtgag ccttgtgaca cagaggagcc tgggggacct gatcatgagc tgctgccccg acccaaaccc acccatccac aagatcgtga gaaaaccctc cagaatcctc ttcctcatgg acggcttcga tgagctgcaa ggtgcctttg acgagcacat aggaccgctc tgcactgact ggcagaaggc cgagcgggga gacattctcc tgagcagcct catcagaaag aagctgcttc ccgaggcctc tctgctcatc accacgagac ctgtggccct ggagaaactg cagcacttgc tggaccatcc tcggcatgtg gagatcctgg gtttctccga ggccaaaagg aaagagtact tcttcaagta cttctctgat gaggcccaag ccagggcagc cttcagtctg attcaggaga acgaggtcct cttcaccatg tgcttcatcc ccctggtctg ctggatcgtg tgcactggac tgaaacagca gatggagagt ggcaagagcc ttgcccagac atccaagacc accaccgcgg tgtacgtctt cttcctttcc agtttgctgc agccccgggg agggagccag gagcacggcc tctgcgccca cctctggggg ctctgctctt tggctgcaga tggaatctgg aaccagaaaa tcctgtttga ggagtccgac ctcaggaatc atggactgca gaaggcggat gtgtctgctt cctgaggat gaacctgttc caaaaggaag tggactgcga gaagttctac agcttcatcc acatgacttt ccaggagttc tttgccgcca tgtactacct gctggaagag gaaaaggaag gaaggacgaa cgttccaggg agtcgtttga agcttcccag ccgagacgtg acagtccttc tggaaaacta tggcaaattc gaaaaggggt atttgatttt tgttgtacgt ttcctctttg gcctggtaaa ccaggagagg acctcctact tggagaagaa attaagttgc aagatctctc agcaaatcag gctggagctg ctgaaatgga ttgaagtgaa agccaaagct aaaaagctgc agatccagcc cagccagctg gaattgttct actgtttgta cgagatgcag gaggaggact tcgtgcaaag ggccatggac tatttcccca agattgagat caatctctcc accagaatgg accacatggt ttcttccttt tgcattgaga actgtcatcg ggtggagtca ctgtccctgg ggtttctcca taacatgccc aaggaggaag aggaggagga aaaggaaggc cgacaccttg atatggtgca gtgtgtcctc ccaagctcct ctcatgctgc ctgttctcat gg
```

Nlrp3 siRNAs of the present technology can be constructed using chemical synthesis and enzymatic ligation reactions using procedures known in the art. For example, a siRNA can be chemically synthesized using naturally occurring nucleotides or modified nucleotides designed to increase the biological stability of the molecules or to increase the physical stability of the duplex formed between the antisense and sense nucleic acids, e.g., phosphorothioate derivatives and acridine substituted nucleotides.

Additionally or alternatively, in some embodiments, one or more nucleobases of the Nlrp3 siRNAs of the present technology may be substituted with a modified nucleobase selected from among 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 3'-amino-2'-deoxy-2,6-Diaminopurine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine, 7-deazaguanosine, 2-aminopyridine and 2-pyridone. In certain embodiments, one or more nucleobases of the Nlrp3 siRNAs of the present technology may be substituted with a modified nucleobase selected from among 5-fluorouracil, 5-bromouracil, 5-chlorouracil, 5-hodouracil, hypoxanthine, xanthine, 4-acetylcytosine, 5-(carboxyhydroxylmethyl)uracil, 5-carboxymethylaminomethyl-2-thouridine, 5-carboxymethylaminometh-yluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-metnylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutosine, pseudouracil, queosine, 2-thiocytosine, 5-methyl-2-thiouracil, 2-thlouracil, 4-thiouracil, 5-methyluracil, uracil-5-oxyacetic acid methylester, uracil-5-cxyacetic acid (v), 5-methyl-2-thiouracil, 3-(3-amino-3-N-2-carboxypropyl) uracil, (acp3)w, and 2,6-diaminopurine.

In some embodiments, one or more nucleobases of the Nlrp3 siRNAs of the present technology may be substituted with a modified nucleobase selected from among tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one),
G-clamps such as a substituted phenoxazine cytidine (e.g., 9-(2-am-oelhoxy)-H-pyrimido[5,4-b][1,4]benzoxazin-2 (3H)-one), carbazole cytidine (2H-pyrimido[4,5-b]indol-2-one), pyridoindole cytidine (H-pyrido[3,2,5]pyrrolo[2,3-d] pyrimidin-2-one).

Additionally or alternatively, in some embodiments, the sugars of one or more nucleobases of the Nlrp3 siRNAs of the present technology may be substituted with modified sugars selected from among 2'-OH (ribose) nucleosides, 2'-O-Methylated (2'-O-Me) nucleosides, 2'-O-methoxyethyl (2'-MOE) nucleosides, 2'-ribo-F nucleosides, 2'-arabino-F nucleosides, 2'-Me nucleosides, and 2'-Me-2'-F nucleosides. In some embodiments, the sugars of one or more nucleobases of the Nlrp3 siRNAs of the present technology may be substituted with modified sugars selected from among 2'-F and 2'-O-alkyl, wherein said O-alkyl is optionally substituted with alkoxy.

In certain embodiments, the siNlrp3/fCNT complex will remain linked at a certain extracellular concentration (e.g., ≥50 nM). However, once the siNlrp3/fCNT complex enters the intracellular environment, the internalization and compartmentalization, along with the loss of undelivered construct through renal elimination, will dilute the concentration to levels where the therapeutic Nlrp3 siRNA will dissociate from the fCNT (e.g., <1 nM). In other embodiments, the therapeutic Nlrp3 siRNA is conjugated to fCNTs via a cleavable sulfide bond that will then be cleaved within the intracellular environment to release the therapeutic Nlrp3 siRNA.

In some embodiments, siNlrp3/fCNTs are prophylactically delivered to specific cell types in the kidney and/or spleen and liver where the fCNTs localize, thereby reducing the damage caused to the organs. In some embodiments, the siNlrp3/fCNTs downregulate target genes thereby ameliorating the damage caused to the kidney and/or spleen. Examples of such genes include, but are not limited to: NLRP3, KIM1, IL-1β, IL-18, HMGB1, CD3, PD-1, IBA1 and/or CC3.

In any embodiment herein, the siNlrp3/fCNTs may have an average molecular weight of about 0.5-100 k, 5-10 k, 5-50 k, 5-100 k, 5-600 k, 100-500 k, 100-400 k, 100-300 k, 100-200 k, 200-600 k, 200-500 k, 200-400 k 200-300 k, 300-600 k, 300-500 k, 300-400 k, 400-600 k, 400-500 k, 0.2-10,000 k, or 500-600 k Dalton. In any embodiment herein, the siNlrp3/fCNTs of the present technology may have an average molecular weight of about 1-500 k, 1-400 k or 2.5-400 k Dalton. In any embodiment herein, the siNlrp3/fCNTs of the present technology may have an average molecular weight of about 300-350 k, about 300 k, or about 350 k Dalton. In any embodiment herein, the siNlrp3/fCNTs may exhibit rapid blood clearance (e.g., $t_{1/2}$ of about 120, 100, 90, 75, 60, 45, 30, 15, 12, 10, 9, 8, 7, 6, 5, 4, 3, 2, or 1 min.); minimal kidney and/or spleen accumulation; and/or renal elimination of 1-100%, 50-60%, 60-70%, 70-80%, 80-90%, or over 90% of the injected dose within one hour of intravenous administration.

Therapeutic Methods

The following discussion is presented by way of example only, and is not intended to be limiting.

One aspect of the present technology includes methods of treating a disease or condition characterized by elevated expression levels and/or increased activity of NLRP3. Additionally or alternatively, in some embodiments, the present technology includes methods of treating renal injury and CKD. In one aspect, the present disclosure provides a method for inhibiting kidney cell fibrosis and inflammation in a subject in need thereof, comprising administering to the subject a therapeutically effective amount of at least one siNlrp3/fCNT, wherein the subject suffers from a disease or condition characterized by elevated expression levels and/or increased activity of NLRP3. In some embodiments, the subject is diagnosed as having, suspected as having, or at risk of having a disease or condition characterized by elevated expression levels and/or increased activity of NLRP3. Additionally or alternatively, in some embodiments, the subject is diagnosed as having CKD.

In therapeutic applications, compositions or medicaments comprising a siNlrp3/fCNT disclosed herein are administered to a subject suspected of, or already suffering from such a disease or condition (such as, a subject diagnosed with a disease or condition characterized by elevated expression levels and/or increased activity of NLRP3 and/or a subject diagnosed with CKD), in an amount sufficient to cure, or at least partially arrest, the symptoms of the disease, including its complications and intermediate pathological phenotypes in development of the disease.

Subjects suffering from a disease or condition characterized by elevated expression levels and/or increased activity of NLRP3 and/or a subject diagnosed with CKD can be identified by any or a combination of diagnostic or prognostic assays known in the art. For example, typical symptoms of CKD include, but are not limited to, metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritus, and ecchymosis.

In some embodiments, subjects with a disease or condition characterized by elevated expression levels and/or increased activity of NLRP3, and/or subjects suffering from CKD that are treated with the siNlrp3/fCNT will show amelioration or elimination of one or more of the following symptoms: metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis.

In certain embodiments, subjects with a disease or condition characterized by elevated expression levels and/or increased activity of NLRP3, and/or subjects suffering from CKD that are treated with the siNlrp3/fCNT will show reduced kidney cell fibrosis and inflammation and/or increased survival compared to untreated CKD subjects. In certain embodiments, subjects with a disease or condition characterized by elevated expression levels and/or increased activity of NLRP3, and/or subjects suffering from CKD that are treated with the siNlrp3/fCNT will show reduced NLRP3, KIM1, IL-1β, IL-18, HMGB1, CD3, PD-1, IBA1 and/or CC3 expression levels compared to that observed in untreated CKD subjects.

In one aspect, the present disclosure provides a method for monitoring the therapeutic efficacy of a siNlrp3/fCNT in a subject diagnosed with CKD comprising: (a) detecting NLRP3 protein levels in a test sample obtained from the subject after the subject has been administered the siNlrp3/fCNT; and (b) determining that the siNlrp3/fCNT is effective when the NLRP3 protein levels in the test sample are reduced compared to that observed in a control sample obtained from the subject prior to administration of the siNlrp3/fCNT. The test sample may be tissues, cells or biological fluids (blood, plasma, saliva, urine, serum etc.) present within a subject. Alternatively, KIM1, serum creatinine, BUN, or other injury biomarker expression levels may be used to determine efficacy of the siNlrp3/fCNT in the subject (see Example 5 described herein). Accordingly, in certain embodiments, the method further comprises detecting expression levels of KIM1 in the subject, wherein a decrease in KIM1 expression levels relative to those observed in the subject prior to treatment is indicative of the therapeutic efficacy of the siNlrp3/fCNT.

Prophylactic Methods

In one aspect, the present technology provides a method for preventing or delaying the onset or progression of a disease or condition characterized by elevated expression levels and/or increased activity of NLRP3. Additionally or alternatively, in some aspects, the present technology provides a method for preventing or delaying the onset or progression of renal injury and/or CKD.

In prophylactic applications, pharmaceutical compositions or medicaments comprising a siNlrp3/fCNT disclosed herein are administered to a subject susceptible to, or otherwise at risk of a disease or condition characterized by elevated expression levels and/or increased activity of NLRP3, and/or a subject susceptible to, or otherwise at risk of CKD, in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic siNlrp3/fCNT can occur prior to the manifestation of symptoms characteristic of the disease or disorder, such that the disease or disorder is prevented or, alternatively, delayed in its progression.

In some embodiments, treatment with the siNlrp3/fCNT will prevent or delay the onset of one or more of the following symptoms: metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis. In certain embodiments, (a) subjects with a disease or condition characterized by elevated expression levels and/or increased activity of NLRP3, and/or (b) subjects with CKD that are treated with the siNlrp3/fCNT will show NLRP3 and/or KIM1 expression levels that resemble those observed in healthy control subjects.

For therapeutic and/or prophylactic applications, a pharmaceutical composition comprising a siNlrp3/fCNT disclosed herein, is administered to the subject. In some embodiments, the siNlrp3/fCNT is administered one, two, three, four, or five times per day. In some embodiments, the siNlrp3/fCNT is administered more than five times per day. Additionally or alternatively, in some embodiments, the siNlrp3/fCNT is administered every day, every other day, every third day, every fourth day, every fifth day, or every sixth day. In some embodiments, the siNlrp3/fCNT is administered weekly, bi-weekly, tri-weekly, or monthly. In some embodiments, the siNlrp3/fCNT is administered for a period of one, two, three, four, or five weeks. In some embodiments, the siNlrp3/fCNT is administered for six weeks or more. In some embodiments, the siNlrp3/fCNT is administered for twelve weeks or more. In some embodiments, the siNlrp3/fCNT is administered for a period of less than one year. In some embodiments, the siNlrp3/fCNT is administered for a period of more than one year. In some embodiments, the siNlrp3/fCNT is administered throughout the subject's life.

In some embodiments of the methods of the present technology, the siNlrp3/fCNT is administered daily for 1 week or more. In some embodiments of the methods of the present technology, the siNlrp3/fCNT is administered daily for 2 weeks or more. In some embodiments of the methods of the present technology, the siNlrp3/fCNT is administered daily for 3 weeks or more. In some embodiments of the methods of the present technology, the siNlrp3/fCNT is administered daily for 4 weeks or more. In some embodiments of the methods of the present technology, the siNlrp3/fCNT is administered daily for 6 weeks or more. In some embodiments of the methods of the present technology, the siNlrp3/fCNT is administered daily for 12 weeks or more. In some embodiments, the siNlrp3/fCNT is administered daily throughout the subject's life.

Determination of the Biological Effect of siNlrp3/fCNTs

In various embodiments, suitable in vitro or in vivo assays are performed to determine the effect of a specific siNlrp3/fCNT and whether its administration is indicated for treatment. In various embodiments, in vitro and in vivo assays can be performed with representative cell lines and animal models, respectively, to determine if a given siNlrp3/fCNT exerts the desired effect on reducing or eliminating signs and/or symptoms of CKD. Compounds for use in therapy can be tested in suitable animal model systems including, but not limited to rats, mice, chicken, canines, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more siNlrp3/fCNTs.

Animal models of CKD may be generated using techniques known in the art. Such models may be used to demonstrate the biological effect of siNlrp3/fCNTs in the prevention and treatment of conditions arising from disruption of a particular gene, and for determining what comprises a therapeutically effective amount of the one or more siNlrp3/fCNTs disclosed herein in a given context.

Modes of Administration and Effective Dosages

Any method known to those in the art for contacting a cell, organ or tissue with one or more siNlrp3/fCNTs disclosed herein may be employed. Suitable methods include in vitro, ex vivo, or in vivo methods. In vivo methods typically include the administration of one or more siNlrp3/fCNTs to a mammal, suitably a human. When used in vivo for therapy, the one or more siNlrp3/fCNTs described herein are administered to the subject in effective amounts (i.e., amounts that have desired therapeutic effect). The dose and dosage regimen will depend upon the degree of the disease state of the subject, the characteristics of the particular siNlrp3/fCNT used, e.g., its therapeutic index, and the subject's history.

The effective amount may be determined during preclinical trials and clinical trials by methods familiar to physicians and clinicians. An effective amount of one or more siNlrp3/fCNTs useful in the methods may be administered to a mammal in need thereof by any of a number of well-known methods for administering pharmaceutical compounds. The siNlrp3/fCNTs may be administered systemically or locally.

The one or more siNlrp3/fCNTs described herein can be incorporated into pharmaceutical compositions for administration, singly or in combination, to a subject for the treatment or prevention of CKD. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more siNlrp3/fCNTs disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that absorption delays, for example, aluminum monostearate or gelatin or protein or liposome.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother,* 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more siNlrp3/fCNTs disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10, 000 micrograms per kg body weight. In one embodiment, one or more siNlrp3/fCNT concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more siNlrp3/fCNTs may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy

In some embodiments, the one or more siNlrp3/fCNTs disclosed herein may be separately, sequentially or simultaneously administered with at least one additional therapeutic agent selected from the group consisting of angiotensin-converting enzyme (ACE) inhibitors, angiotensin II receptor blockers, beta-blockers, calcium channel blockers, renin inhibitors, diuretics, erythropoietin, and any combination thereof.

Examples of angiotensin-converting enzyme (ACE) inhibitors include benazepril, captopril, enalapril, ramipril, lisinopril, and mixtures thereof.

Examples of angiotensin II receptor blockers include azilsartan, candesartan, eprosartan, irbesartan, losartan, olmesartan, telmisartan, valsartan, and mixtures thereof.

Examples of beta-blockers include atenolol, carvedilol, metoprolol, propranolol, and mixtures thereof.

Examples of calcium channel blockers include amlodipine, diltiazem, felodipine, isradipine, nicardipine, nifedipine, nisoldipine, verapamil, and mixtures thereof.

Examples of renin inhibitors include pepstatin, CGP2928, aliskiren, and mixtures thereof.

Examples of diuretics include chlorthalidone, chlorthiazide, hydrochlorthiazide, indapamide, metolazone, amiloride, bumetanide, furosemide, spironolactone, triamterene, and mixtures thereof.

In certain embodiments, an additional therapeutic agent is administered to a subject in combination with the one or more siNlrp3/fCNTs disclosed herein such that a synergistic therapeutic effect is produced. For example, administration of one or more siNlrp3/fCNTs with one or more additional therapeutic agents for the prevention or treatment of CKD will have greater than additive effects in the prevention or treatment of the disease. For example, lower doses of one or more of the therapeutic agents may be used in treating or preventing CKD resulting in increased therapeutic efficacy and decreased side-effects. In some embodiments, the one or more siNlrp3/fCNTs disclosed herein are administered in combination with any of the at least one additional therapeutic agents described above, such that a synergistic effect in the prevention or treatment of CKD results.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Kits

The present disclosure also provides kits for the prevention and/or treatment of CKD comprising one or more siNlrp3/fCNTs disclosed herein. Optionally, the above described components of the kits of the present technology are packed in suitable containers and labeled for the prevention and/or treatment of CKD.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. The use of the reagents may be according to any embodiment of the methods of the present technology.

EXAMPLES

The present technology is further illustrated by the following Examples, which should not be construed as limiting in any way.

Example 1: Experimental Materials and Methods

Synthesis and Characterization of the Soluble, Functionalized Single Walled Carbon Nanotube Construct: The fCNTs were prepared and characterized via covalent cycloaddition of azomethine ylides with SWCNT, see McDevitt et al., *PloS One*, 2007, 2:e907; McDevitt et al., *Society of Nuclear Medicine*, 2007, 48:1180-1189; Ruggiero et al., *Proc. Nat. Acad. Sci.*, 2010, 107:12369-12374; Alidori, et al., *J. Phys. Chem. C.*, 2013, 117:5982-5992; Villa, et al., *Nano Letters*, 2008, 8:4221-4228. Characterization using different analytical techniques (Transmission Electron Microscopy (TEM), Dynamic-Light-Scattering (DLS), Kaiser assay, RP-HPLC and spectrofluorometric titration with siRNA sequences) revealed an amine content of 0.3 mmol/g of fCNT and chemical purity >99%. Dicer validated RNA sequences (Hefner, et al., *J. Biomol. Tech.*, 2008, 19:231-237) were designed to silence NLR pyrin domain-containing protein 3 (NLRP3). The non-covalent binding of fCNT and siRNA was quantified and the binding affinities were ~5 nmol/L and up to 4 siRNA could be loaded per fCNT under physiological conditions, see Alidori, et al. TEM of solid fCNT and fCNT/siRNA (1:1 complex) was performed and showed a fCNT average length of 300 nm; both samples were water soluble (10 g/L), could be resolved chromatographically, and were rapidly renally filtered in a murine model, see Ruggiero et al. DLS analyses provided evidence in aqueous solution that the molecular lengths of fCNT and fCNT/siRNA (1:1) were comparable and indicated that the assembled drug construct was not an aggregate of cross-linked molecules.

High pressure carbon monoxide (HiPCO) produced single walled carbon nanotubes (SWCNT, >90% purity) were purchased from NanoLab, Inc. (Menlo Park, CA). CoMoCat single wall carbon nanotubes (Sigma-Aldrich or Chasm) have also been ammonium-functionalized and used in vitro and in vivo in these examples and have comparable properties and characteristics. Pristine SWCNT were mildly oxidized in 3M nitric acid (Fisher Scientific, Waltham, MA) to remove metallic impurities. These acid-treated SWCNT were then reacted with the Boc-amine precursor, 2-(2-(2-(2-(tert-butoxycarbonyl)aminoethoxy)ethoxy)ethylamino) acetic acid (Discovery ChemScience LLC, Princeton, N.J.) to yield SWCNT-NHBoc, see Georgakilas et al., *Chem Comm*, 2002, 3050-3051; Alidori et al., *J. Phys. Chem. C.*, 2003, 117:5982-5992. The SWCNT-$NH_2$ product (fCNT) was purified by reverse phase chromatography after deprotecting the Boc-amine. Briefly, the crude fCNT was dissolved in 0.1 M tetraethylammonium acetate ((TEAA), Fisher Scientific, Waltham, MA) and adjusted to pH 7. Acetonitrile (Fisher Scientific, Waltham, MA) was added to a final v/v of 20%. A Seppak Plus C18 cartridge (Waters Corp., Milford, MA) was equilibrated with 20% acetonitrile/ 0.1 M TEAA. The SWCNT-$NH_2$ was loaded onto the cartridge and washed extensively with 20% acetonitrile/0.1 M TEAA at 1 mL/min. The purified SWCNT-$NH_2$ was eluted from the cartridge in 50% acetonitrile/water and the solvent evaporated to yield the purified SWCNT-$NH_2$ solid. Purity and identity of the fCNT were assessed by UV-Vis spectroscopy, HPLC, transmission electron microscopy (TEM) and dynamic light scattering (DLS), see Alidori et al. Analytical HPLC was performed on a Beckman Coulter System Gold chromatography system equipped with in-line UV/Vis spectrum detector and tunable multi-wavelength fluorescence detector (Jasco FP-2020). The stationary phase was a Gemini (Phenomenex, Torrence, CA) C18 column (5μ, 250×4.6 mm) column. A 0-to-100% mobile phase gradient of 0.1M TEAA, pH 6.5 and acetonitrile was used at a flow rate of 1.0 mL/min for 30 minutes. TEM analysis was performed using 200 mesh grids coated with carbon support film and viewed on a JEOL JEM 1400 TEM with a LaB6 filament. Images were taken using an Olympus SIS Veleta 2 k×2 k side mount camera. DLS was performed using a Zetasizer Nano ZS system equipped with a narrow bandwidth filter (Malvern Instruments Inc, Westborough, MA).

siRNA Sequences: Dicer validated RNA sequences (Hefner, et al., *J. Biomol. Tech.*, 2008, 19:231-237) were designed to silence NLR pyrin domain-containing protein 3 (NLRP3). Other RNA sequence pairs with chains having lengths ranging from 9 to 45 bases (synthethetic or natural base or linkage composition) can bind to the fCNT and are applicable candidates. The following (sense (s) and antisense (as)) sequences were used:

(SEQ ID NO: 3)
siNlrp3: 5' CUUUCCCAAAAUUGAGAUCAACCTC 3' (s),

SEQ ID NO: 4)
siNlrp3: 5' GAGGUUGAUCUCAAUUUUGGGAAAGUG 3' (as).

Quantitative Polymerase Chain Reaction: At the time mice were sacrificed, entire kidneys were frozen and kept at −80° C. RNA was isolated and reverse-transcribed using the SuperScript III First-Strand Synthesis system (ThermoFisher Scientific, Waltham, MA). Quantitative PCR was performed using QuantiTect SYBR Green PCR dye (Qiagen, Valencia, CA) and the ABI General System 7300 (ABI Applied System, University Park, IL). PCR conditions were:

| | | |
|---|---|---|
| 95° C. | 3 minutes | 1 cycle |
| 95° C. | 30 seconds | 35 cycles |
| 55° C. | 30 seconds | |
| 72° C. | 30 seconds | |

The following primers were used: IL18 (Mm00434226_m1), Havcr1 (Mm00506686_m1), IL1β (Mm00434228-m1), Nlrp3 (Mm00840904_m1), Hmox1 (Mm00516005_m1), GAPDH (4351309) all were acquired from Applied Biosystems (Foster City, CA).

Immunohistochemical and Immunofluorescence Staining: The immunohistochemistry detection of CD3, Iba1, CC3, PD-1, Ki67, CD8, CD11b, CD4, FOXP3 and F4/80 was performed using Discovery XT processor (Ventana Medical Systems, Oro Valley, AZ). The tissue sections were blocked for 30 minutes in 10% normal goat serum, 2% BSA in PBS. Table 1 lists the concentrations for each of the primary antibodies. The samples were incubated with the respective primary antibodies for 5 hours, followed by 60 minutes incubation with biotinylated goat anti-rabbit IgG (Vector labs, cat #:PK6101) or the proper biotinylated anti-rat or anti-goat secondary antibody in 1:200 dilution. Blocker D, Streptavidin-HRP, DAB detection kit (Ventana Medical Systems, Oro Valley, AZ), and Tyramide-Alex Fluor 488 (Invitrogen, Carlsbad, CA) were used according to the manufacturer instructions.

TABLE 1

Antibodies used in immunohistochemical and immunofluorescence analysis.

| Ab | Species | Mono/ Polyclonal | Company | Cat. no. | Conc. (μg/mL) |
|---|---|---|---|---|---|
| CD3 | Rb | poly | Dako | A0452 | 1.2 |
| IBA1 | Rb | Poly | Wako | 091-19741 | 0.5 |
| CC3 | Rb | Poly | Cell Sign. | 9661 | 0.1 |
| PD1 | Rb | Poly | Sinobiologicals | 50124-rpo2-50 | 1 |

TABLE 1-continued

Antibodies used in immunohistochemical and immunofluorescence analysis.

| Ab | Species | Mono/ Polyclonal | Company | Cat. no. | Conc. (µg/mL) |
|---|---|---|---|---|---|
| Ki67 | Rb | Mono | Abcam | AB16667 | 2.5 |
| CD8 | Rat | Poly | eBiosciences | 14-0808 | 2.5 |
| CD11b | Rb | Poly | Abcam | AB133357 | 0.5 |
| CD4 | Goat | Poly | R&D systems | AF554 | 2 |
| FOXP3 | Rat | Mono | eBiosciences | 14-5773-82 | 0.5 |
| F4/80 | Rat | Mono | Abcam | AB0604 | 2 |

Histopathological Analysis: The kidneys from mice were fixed overnight in 10% formalin or 4% paraformaldehyde overnight followed by processing by standard histological methods and embedded in paraffin. The kidneys were cut into 5 µm sections, and stained with hematoxylin and eosin (H&E). Histopathologic scoring was scored blindly.

Examination of the slides of kidney showed lesions that could be classified into 3 major categories, with one additional minor category:

(1) Tubular damage: Includes acute and chronic processes surrounding tubular damage from direct toxin exposure (folic acid) or indirect processes resulting from a local and/or systemic response to said toxin or other undetermined process. This category also included regenerative processes (e.g., tubular epithelial hyperplasia/hypertrophy).

(2) Interstitial mesenchymal expansion: Includes acute and chronic processes surrounding direct or indirect damage (see above). The term "mesenchymal" includes expansion of the interstitium by cellular components such as fibroblasts, myofibroblasts and/or histiocytes. This category may also include a small number of hypertrophic, hyperplastic or atrophic tubular epithelial cells, which cannot always be readily distinguished without immunohistochemistry.

(3) Mononuclear infiltrates: Includes all mononuclear leukocytes that are present within the interstitium.

(4) Neutrophil infiltrates: Includes degenerate and non-degenerate neutrophils within the interstitium, tubular epithelium and tubular lumen. The classification was developed according to standarized lesions (see Frazier et al., *Toxicologic Pathology,* 2012, 40:14S-86S; Mann et al., *Toxicologic Pathology,* 2012, 40:7S-13S).

Figure 3A:
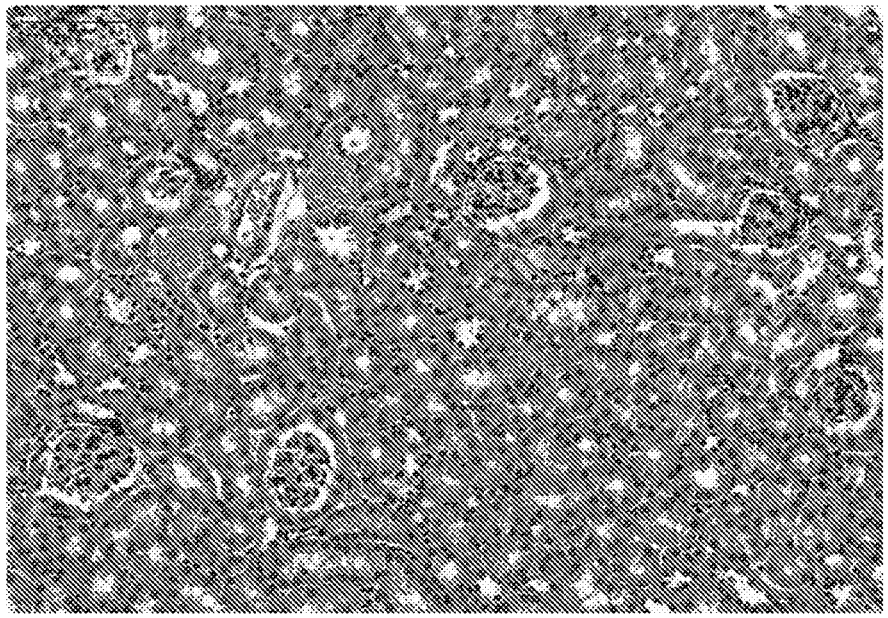
FIGS. 3(A)-3(F) provide histological analysis by hematoxylin and eosin (H&E) staining of kidney samples from mice following FA injury illustrating improved kidney morphology after treatment with the prophylactic siNlrp3/fCNT.
Figure 3B:
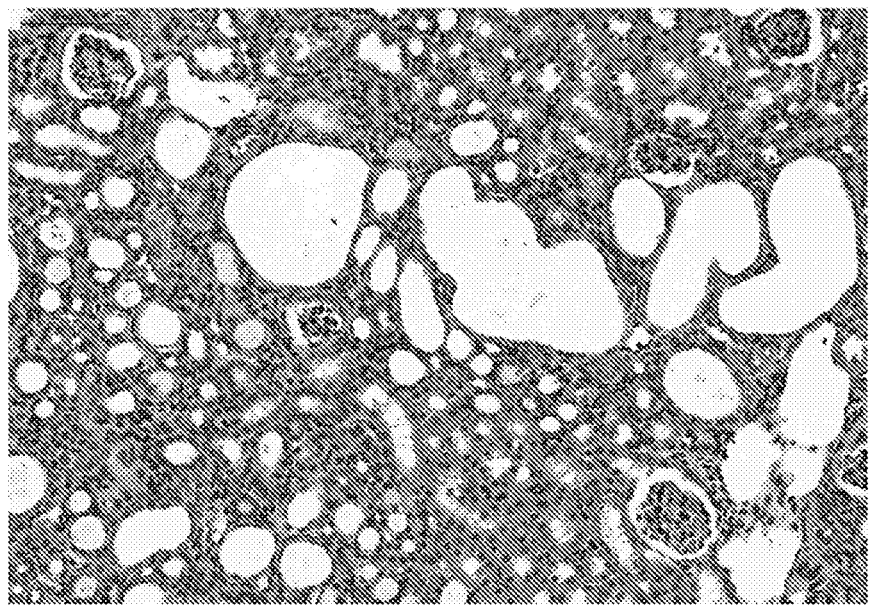
Figure 3C:
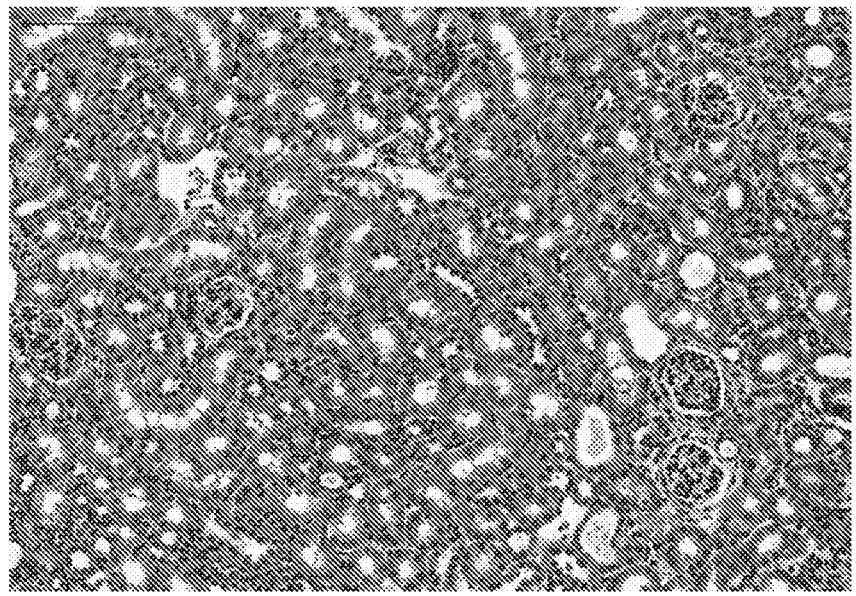
Figure 3D:
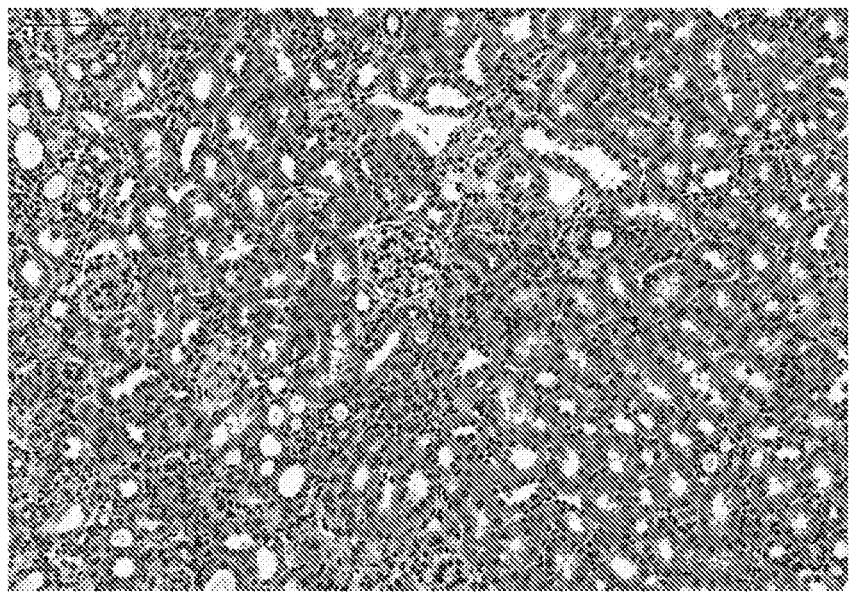
Figure 3E:
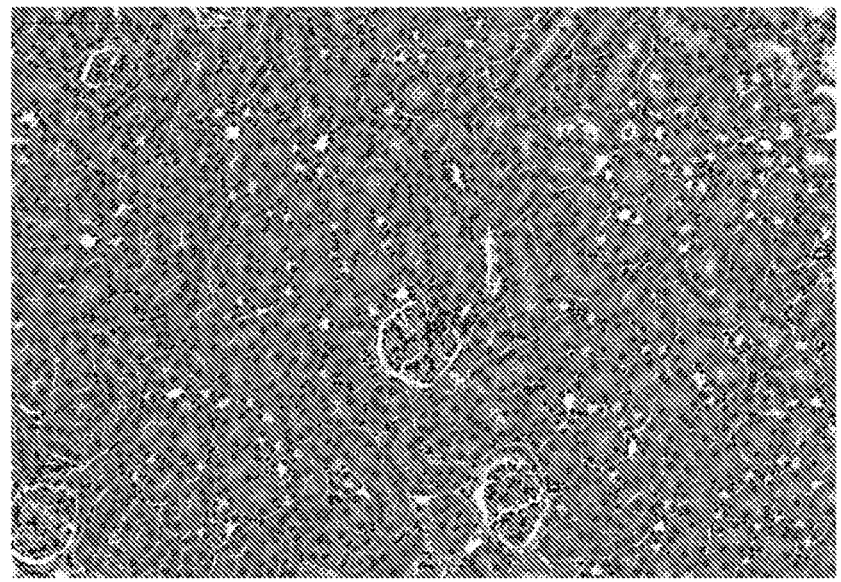
Figure 3F:
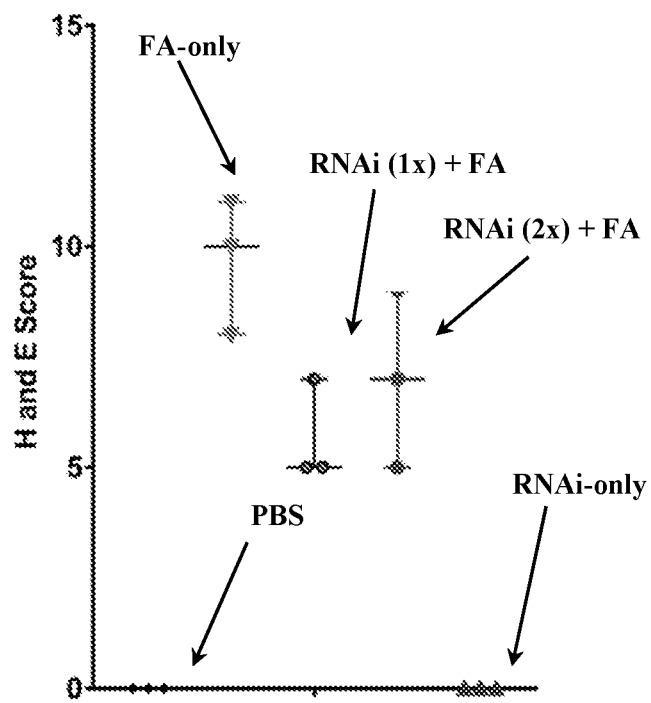

The second step involved the scoring of individual slides according to the grading scheme (FIG. 3(F)). Following scoring, the slides were unblinded and differences were observed between the folic acid-only and the 1×SI and 2×SI treatment groups.

Western Blot Analysis of IL1β and IL18: Cells were lysed with RIPA buffer (25 mM Tris-HCl pH 7.6, 150 mM NaCl, 1% NP-40, 1% sodium deoxychlolate, 0.1% SDS) on ice for 1 hour. Lysates were centrifuged at 13,000×g for 20 minutes. Supernatants were collected and measured for total protein concentration using DC Protein Assay (BioRad, Hercules, CA) according to the manufacturer's instructions. Equal amounts of protein (0.0075 mg) were heated at 95° C. for 5 minutes in 1× Laemlli sample buffer containing 2-mercaptoethanol. SDS-PAGE was carried out at 120 V for 1 hour using 12% acrylamide gels. Electrophoretically separated proteins were transferred to a nitrocellulose membrane at 100 V for 1 hour. Membrane was blocked in 5% non-fat milk in TBST buffer overnight at 4° C. On the following day, the nitrocellulose membranes were incubated with mouse anti-IL1β and IL18 antibodies (Abcam, Cambridge, UK) at 1:5,000 dilution for 1 h at ambient temperature followed by horseradish peroxidase conjugated goat anti-mouse secondary antibodies at 1:20,000 dilution for 1 hour at ambient temperature. Protein bands were detected on X-ray film using an enhanced chemiluminescence system (ChemiDoc MP imaging system, BioRad, Hercules, CA). Glyceraldehyde 3-phosphate dehydrogenase (GAPDH) was included as loading controls and were measured to evaluate protein loading using an anti-GAPDH pAb (R&D Systems, Minneapolis, MN) antibody.

Example 2: Biocompatibility and Non-Toxicity of siNlrp3/fCNT in a Mouse Model of Chronic Kidney Disease To determine if targeted therapy with siNlrp3/fCNT was non-toxic in a mouse model of chronic kidney disease, the change in body weight (%) of treated mice was monitored over time following folic acid administration (FIG. 1). Mice received intraperitoneal (IP) injections of 225 to 250 mg/kg Folic acid (FA) to induce a chronic disease state. siNlrp3/fCNT was delivered to the renal proximal tubule cells 2 days and 7 days after FA injury using sidewall ammonium-functionalized carbon nanotubes (fCNT) as the delivery platform. Control groups included siNlrp3 only to determine the biocompatibility of the treatment in the absence of the FA, naïve animals receiving only vehicle (i.e. no siNlrp3/fCNT or FA), and treatment with FA only.

FIG. 1 shows that the FA only-treated group of animals displayed severe weight loss (>10% decrease from baseline) within 1 week of FA administration. siNlrp3/fCNT-treated mice showed initial weight loss (prior to receiving siNlrp3/fCNT), but subsequently recovered their body weights following siNlrp3/fCNT treatment.

Figure 2A:
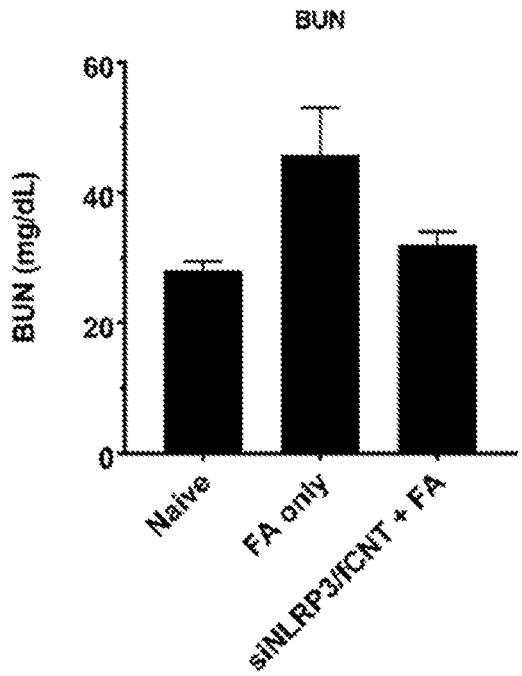
FIGS. 2(A)-2(D) show improvement of biomarker levels of chronic kidney disease through pharmacological intervention with siNlrp3/fCNT.
Figure 2B:
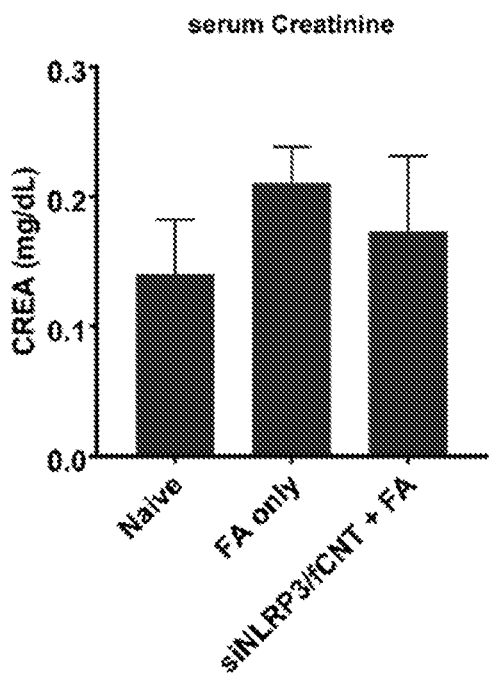
Figure 2C:
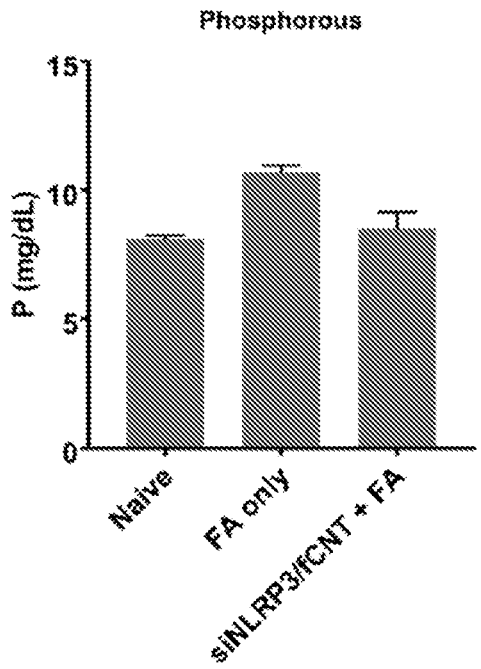
Figure 2D:
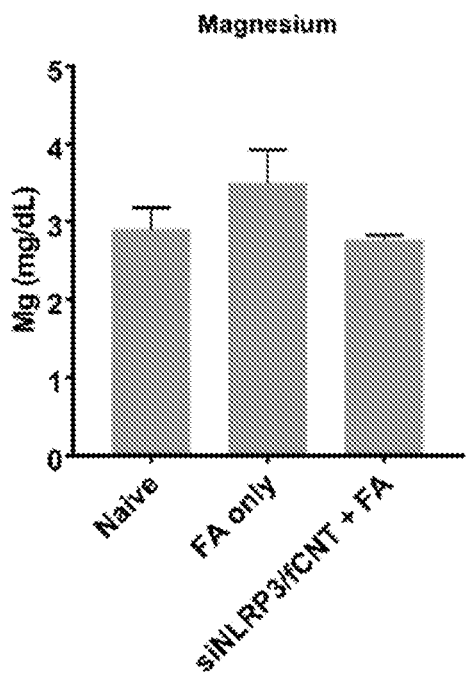

Renal function was assessed using a metabolic panel of blood urea nitrogen (BUN, FIG. 2(A)), serum creatine (FIG. 2(B)), phosphorous (FIG. 2(C)), and magnesium (FIG. 2(D)). As shown in FIGS. 2(A)-2(D), siNlrp3/fCNT treated animals that were exposed to FA injury exhibited decreased levels of blood biomarkers of chronic kidney disease compared to the FA only-treated group.

Accordingly, these results demonstrate that the pharmaceutical compositions of the present technology are useful in methods for treating and/or preventing chronic kidney disease in a subject in need thereof.

Example 3: siNlrp3/fCNT Improves the Overall Health of Chronic Kidney Disease Animals siNlrp3/fCNT treatment successfully minimized symptoms in a chronic kidney disease mouse model. Vehicle treated mice were administered a single dose of PBS and sacrificed on day 14. Folic acid only treated mice were administered a single dose of FA and sacrificed on day 14. FA+siNlrp3/fCNT treated mice were administered FA and one or two doses of siNlrp3/fCNT 48 hours later (mice treated with a single dose of siNlrp3/fCNT were sacrificed on day 7 and mice treated with two doses were sacrificed on day 14). siNlrp3 only treated mice were administered a single dose of siNlrp3 and sacrificed on day 14. All H&E sections were blindly scored using a semi-quantitative scale from 0 to 4 (0=no lesions; 1=minimal lesions; 2=mild lesions; 3=moderate lesions; and 4=marked lesions; FIG. 3(F)).

Histological analysis by hematoxylin and eosin (H&E) staining of kidney samples from mice treated with siNlrp3/fCNT (single dose, sacrificed on day 7; two doses, sacrificed on day 14, siNlrp3 only) following FA injury demonstrated improved tissue morphology that was comparable to healthy control mouse tissue. Compare FIGS. 3(C)-3(D) to FIG. 3(A); see also FIG. 3(F). FA only treated samples (FIG. 3(B)) demonstrated marked lesions in kidney tissue samples compared with healthy control mouse tissue (see FIGS. 3(A) and 3(E)).

Figure 4A:
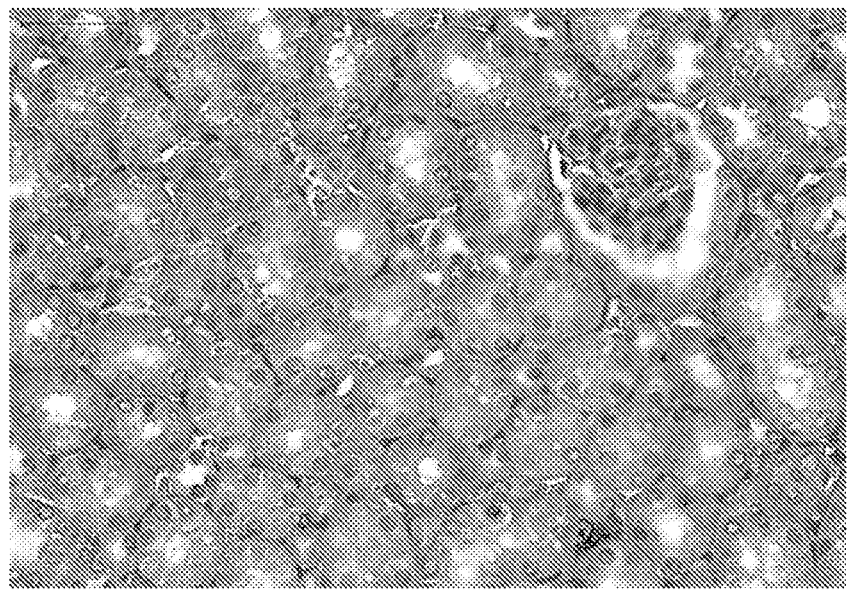
FIGS. 4(A)-4(E) show images used in assessment of renal fibrosis in kidney samples after staining with picrosirius red.
Figure 4B:
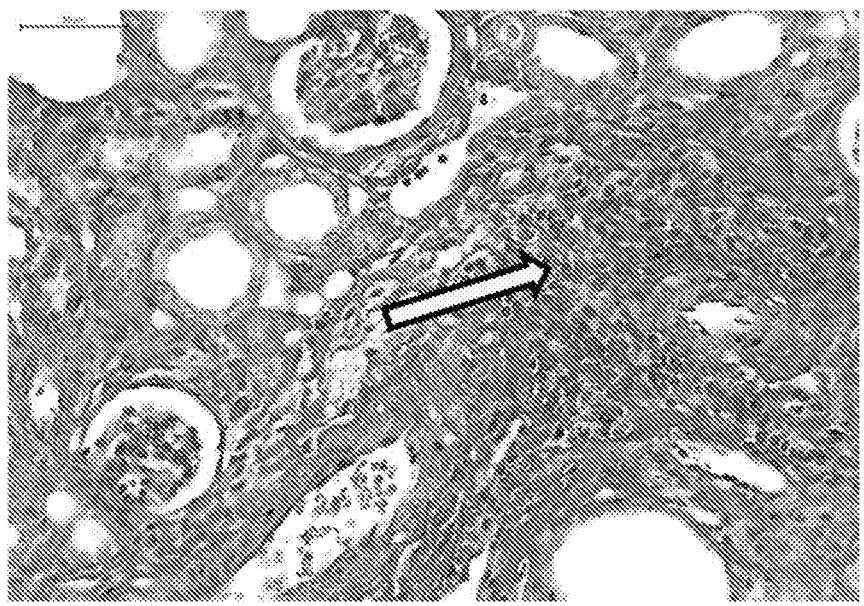
Figure 4C:
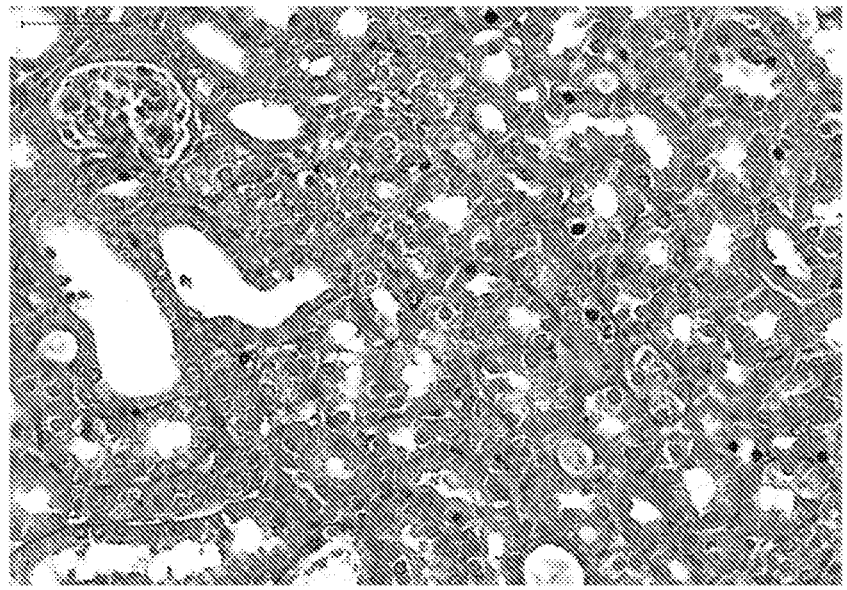
Figure 4D:
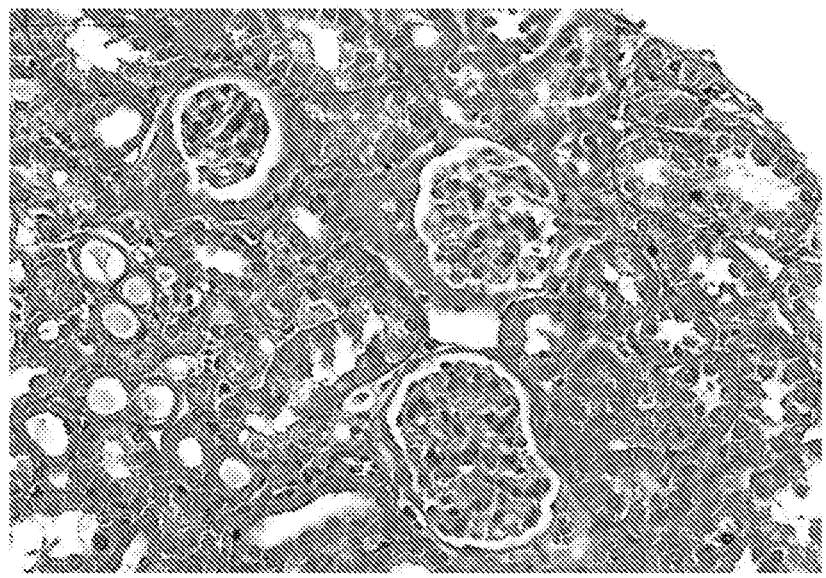
Figure 4E:
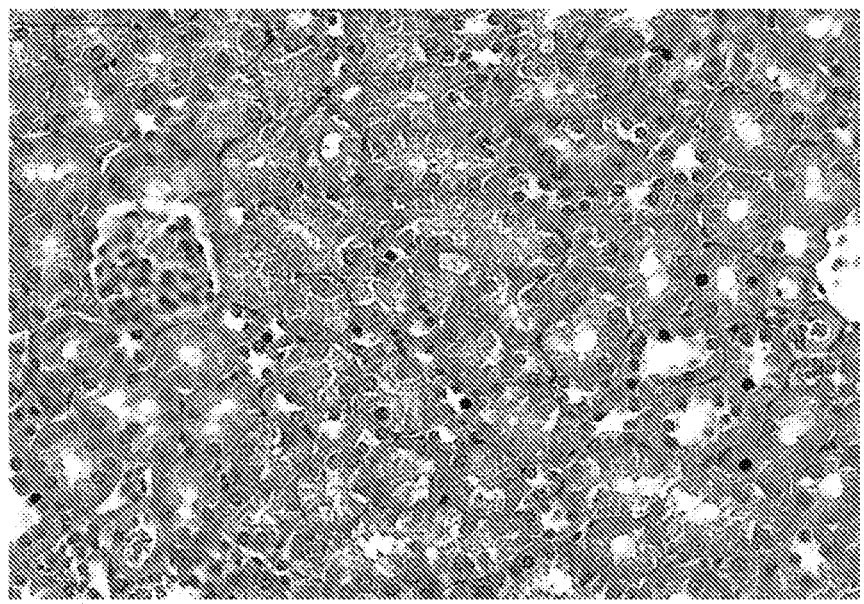

Renal fibrosis was assessed by picrosirius red staining of kidney samples from mice treated with siNlrp3/fCNT following FA injury. siNlrp3/fCNT treated mice following FA injury demonstrated no significant fibrosis and resembled healthy control mouse tissue. Compare FIGS. 4(C)-4(D) to FIGS. 4(A) and 4(E). In the FA only treated group (FIG. 4(B)), significant collagen type I and type III fibril deposits are evident within the interstitial fibrotic lesions.

Figure 5A:
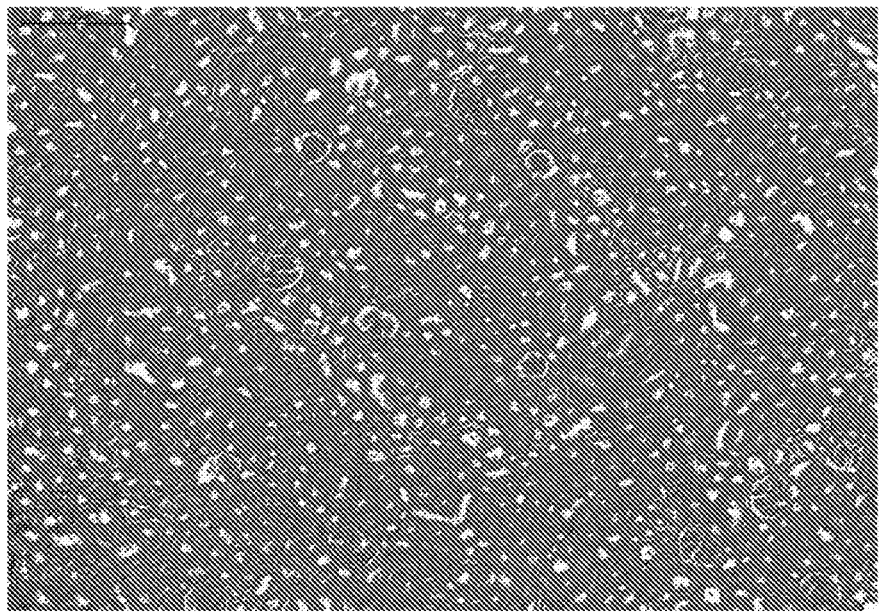
FIGS. 5(A)-5(E) shows images used in assessment of interstitial fibrosis involving Masson Trichrome staining of representative kidney samples.
Figure 5B:
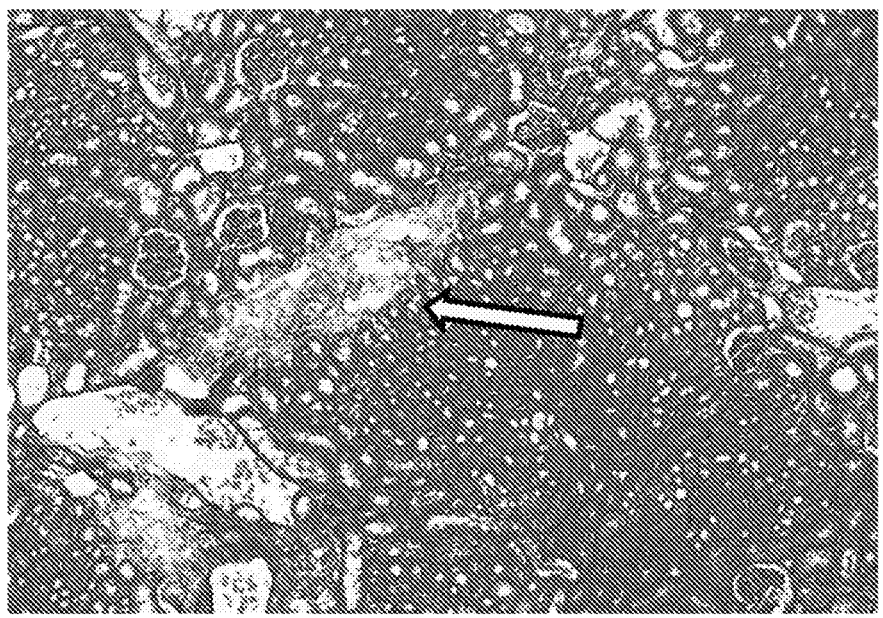
Figure 5C:
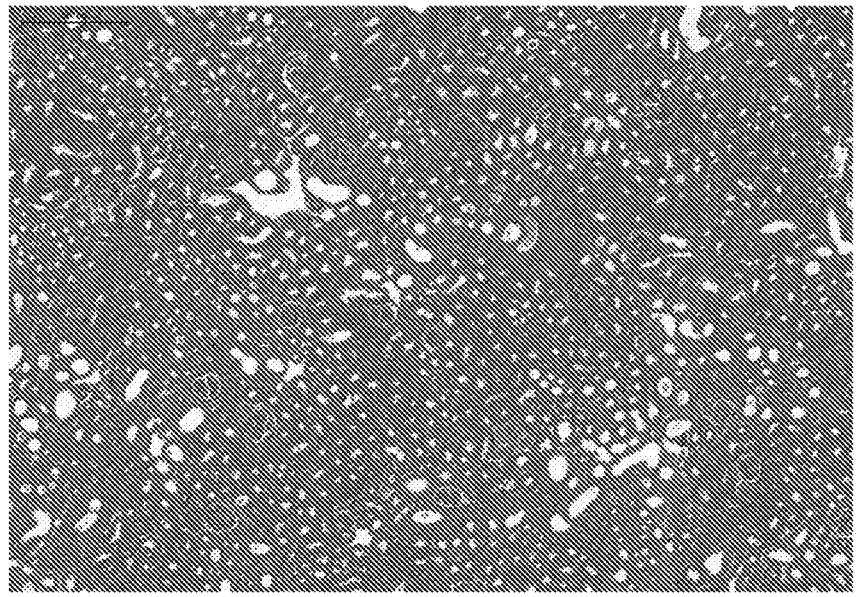
Figure 5D:
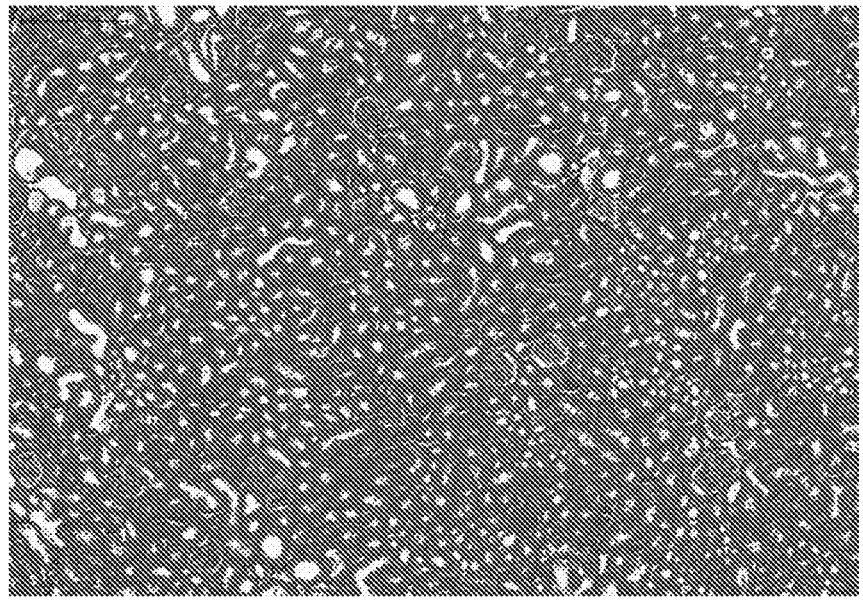
Figure 5E:
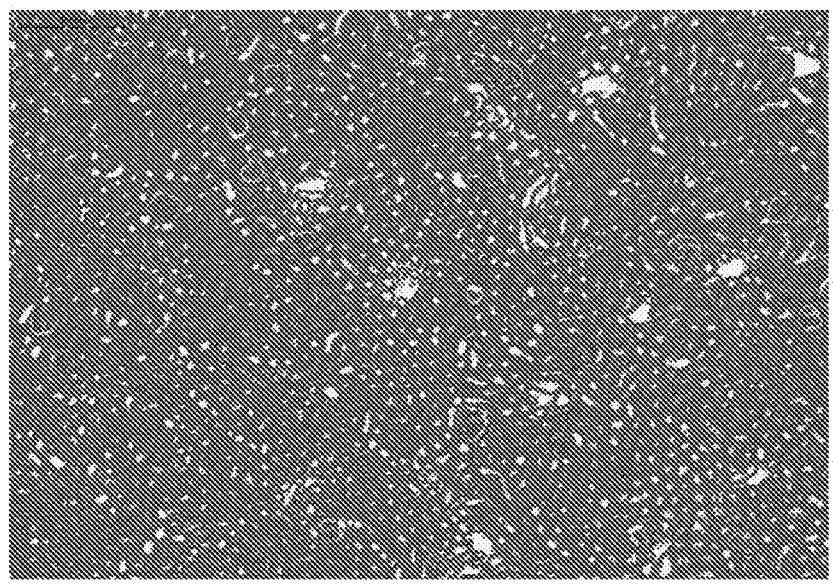

Interstitial fibrosis was confirmed by Masson trichrome staining of the kidney samples from the mice treated with siNlrp3/fCNT following FA injury. siNlrp3/fCNT treated mice following FA injury displayed no significant interstitial fibrosis and resembled healthy mouse tissue. Compare FIGS. 5(C)-5(D) to FIGS. 5(A) and 5(E). FA only treated samples exhibited significant collagen deposits within the interstitial fibrotic lesions (FIG. 5(B)).

Figure 6A:
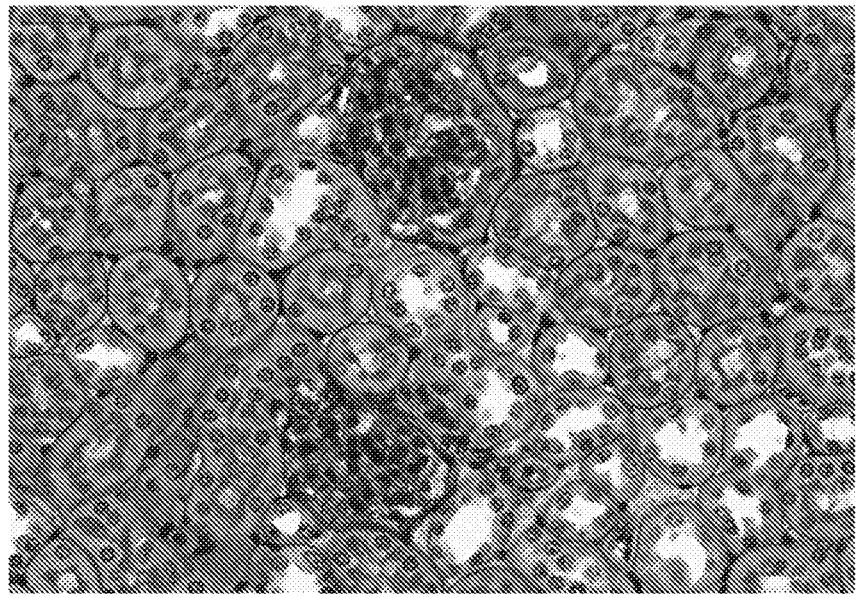
FIGS. 6(A)-6(E) show images from Periodic Acid-Schiff (PAS) staining of representative kidney samples to assess mucopolysaccharide deposits.
Figure 6B:
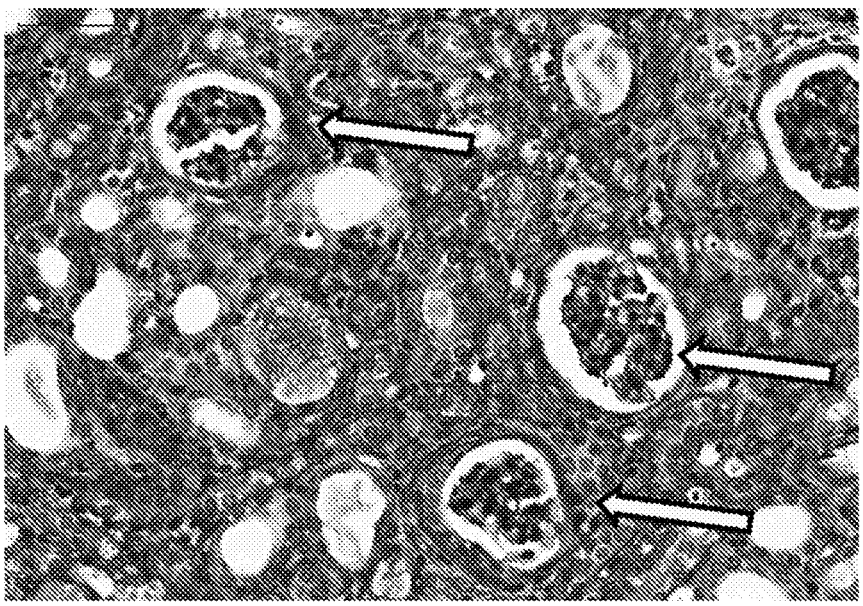
Figure 6C:
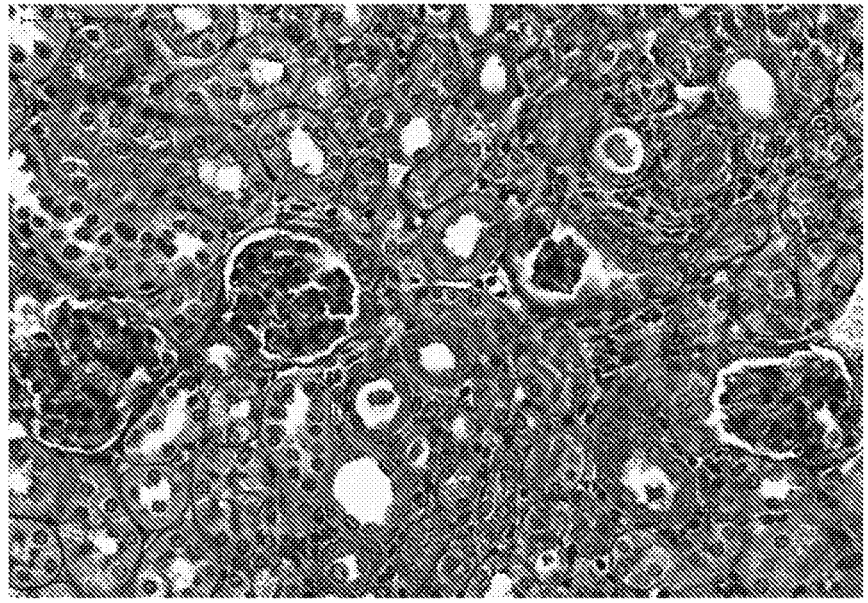
Figure 6D:
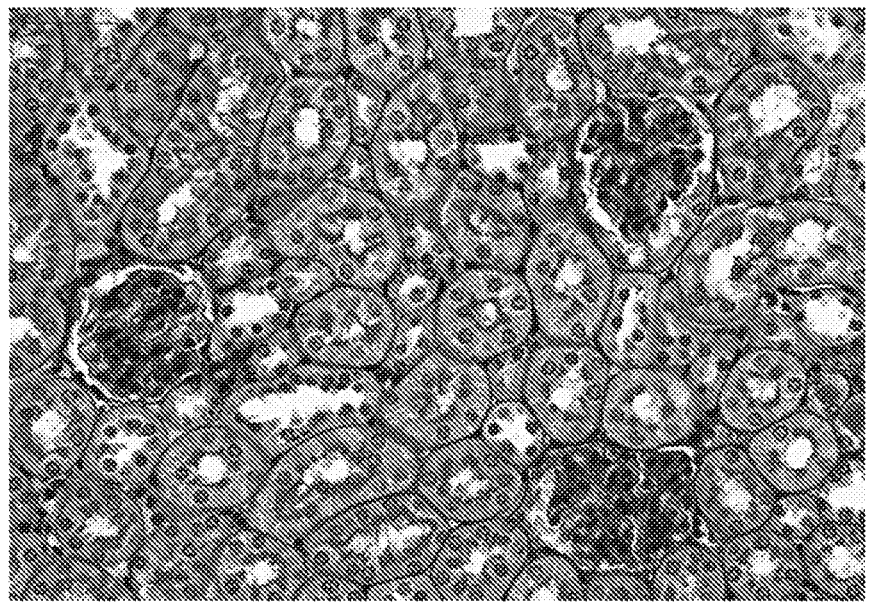
Figure 6E:
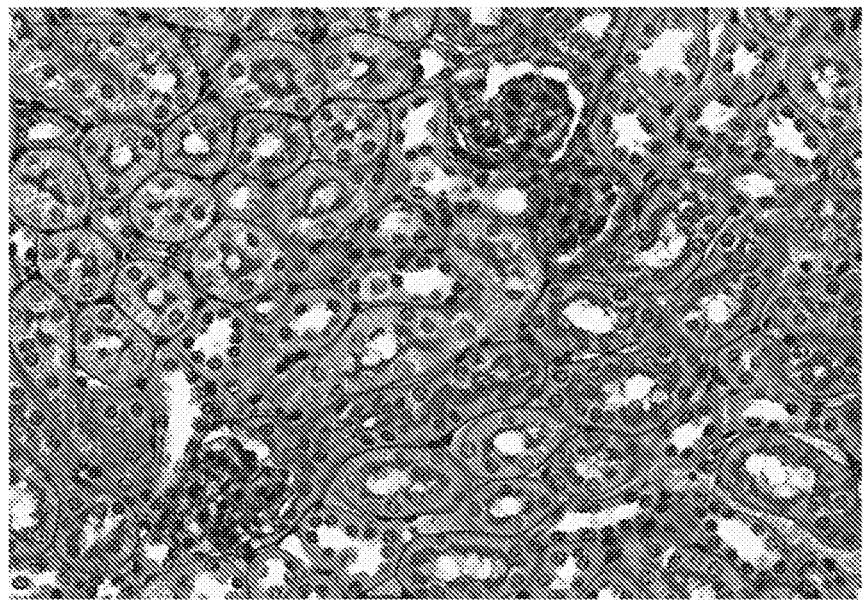
Figure 7A:
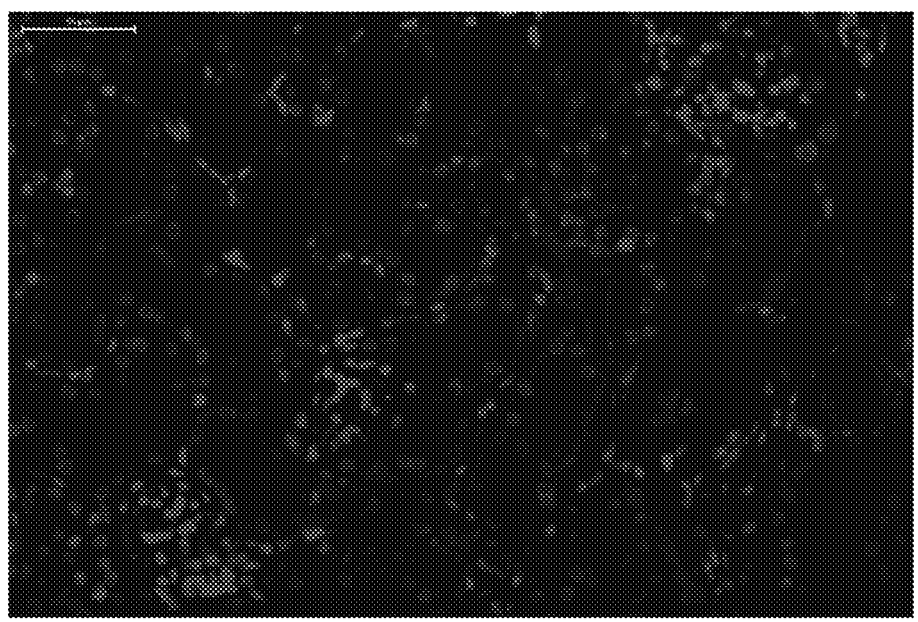
FIGS. 7(A)-7(E) show images from anti-CD3 immunohistological staining of representative kidney samples for T cell infiltration.
Figure 7B:
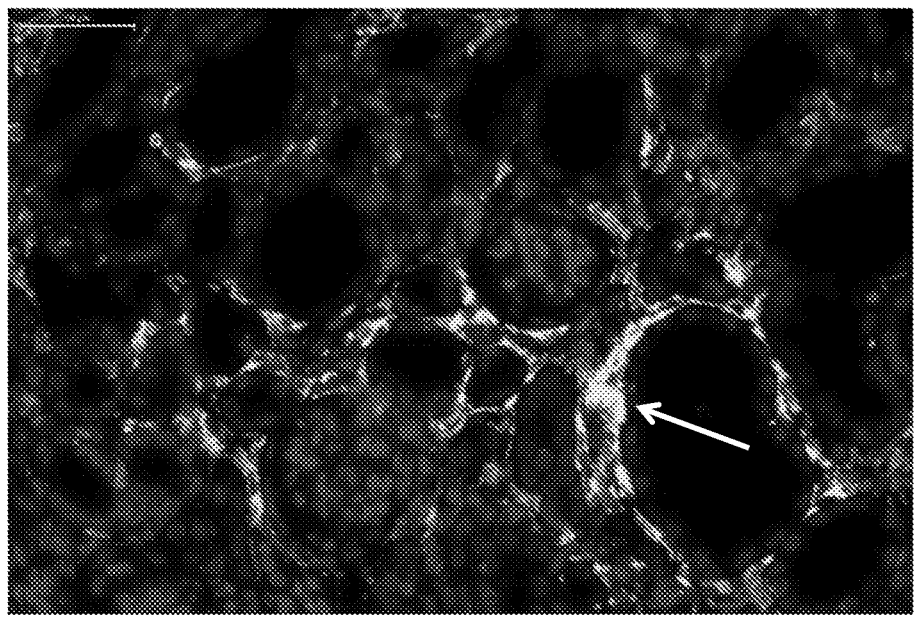
Figure 7C:
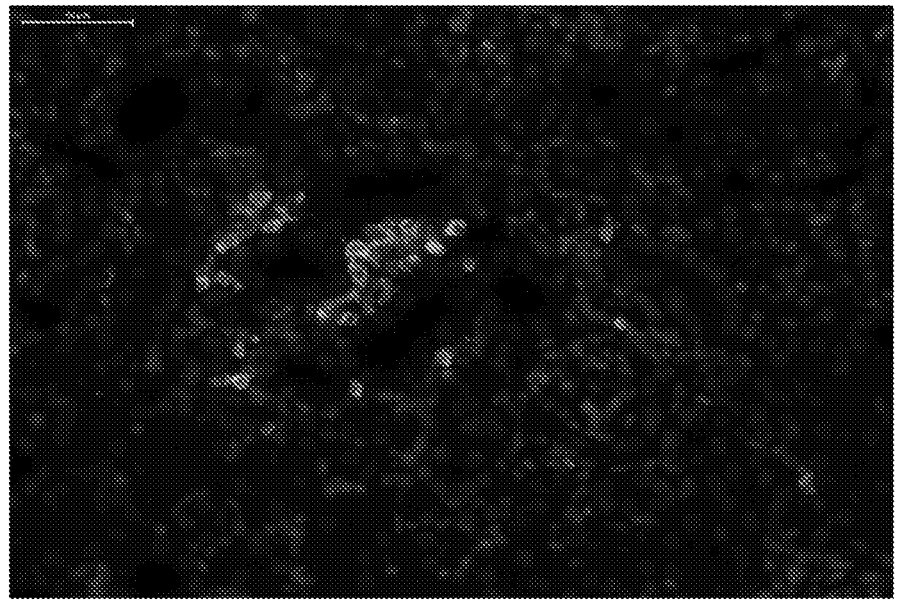
Figure 7D:
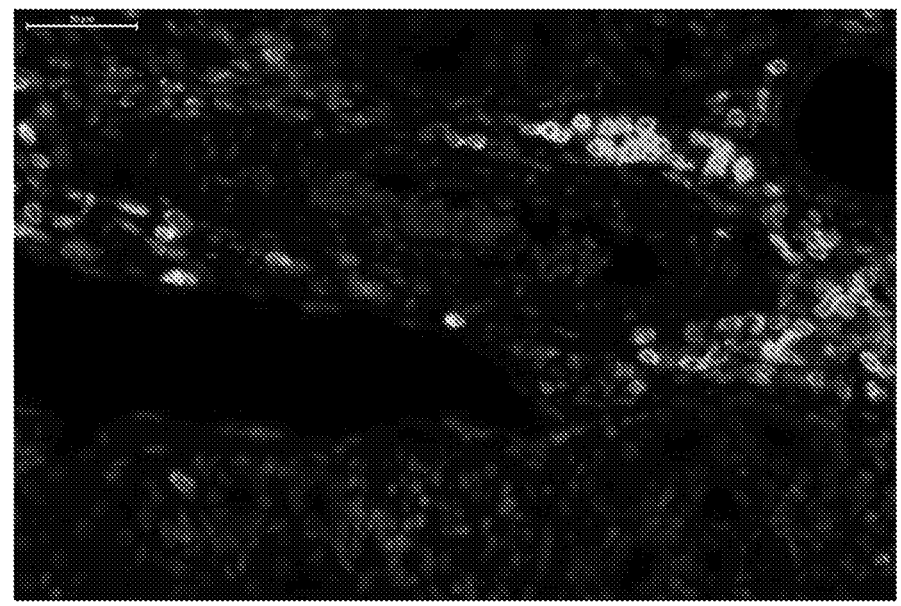
Figure 7E:
Figure 8A:
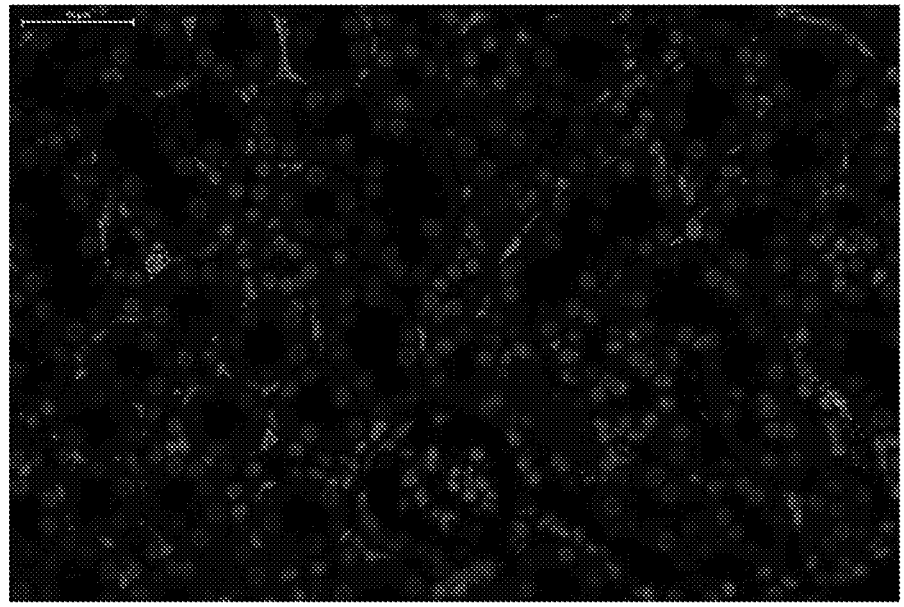
FIGS. 8(A)-8(E) show staining of representative kidney samples for PD-1, a marker of co-inhibitory receptor of lymphocytes.
Figure 8B:
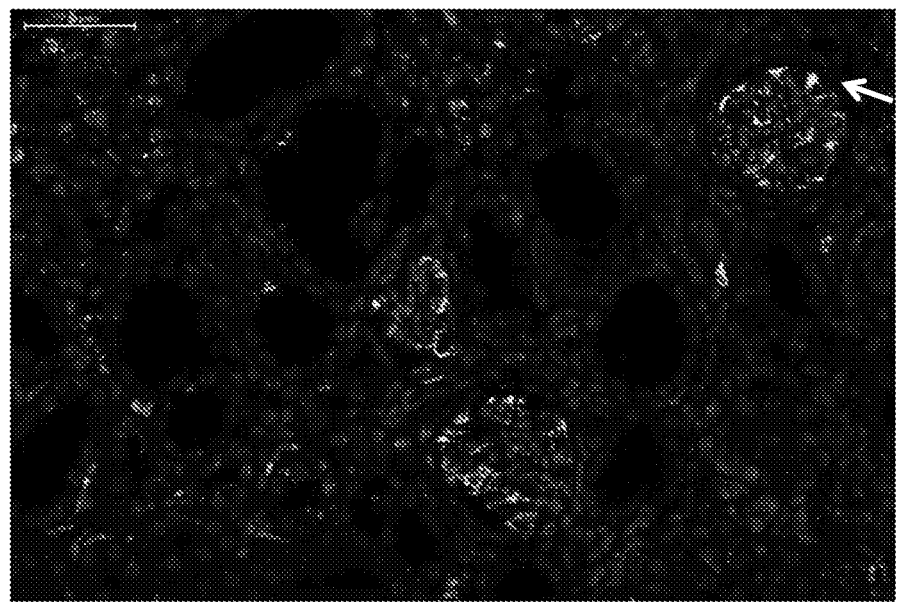
Figure 8C:
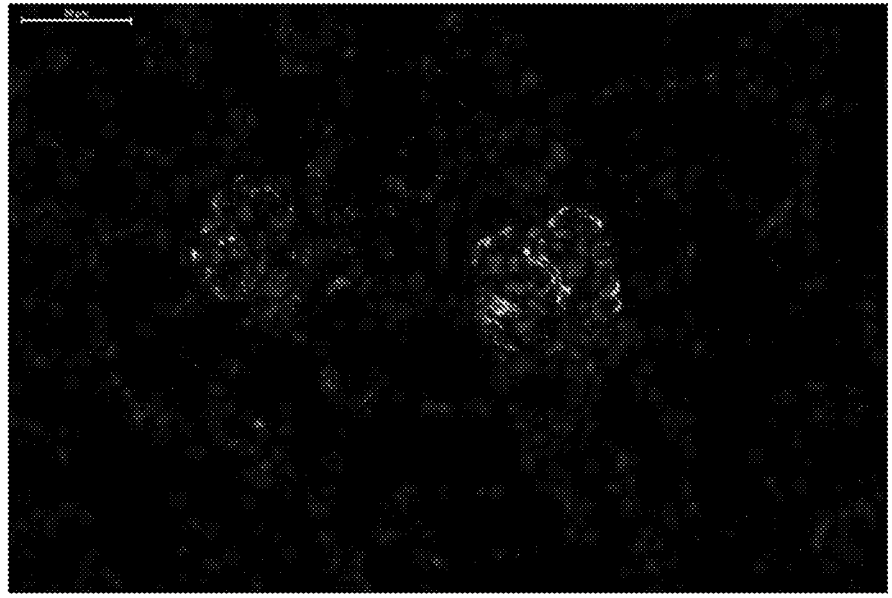
Figure 8D:
Figure 8E:
Figure 9A:
FIGS. 9(A)-9(E) show staining of representative kidney samples with Iba1, a marker of macrophages.
Figure 9B:
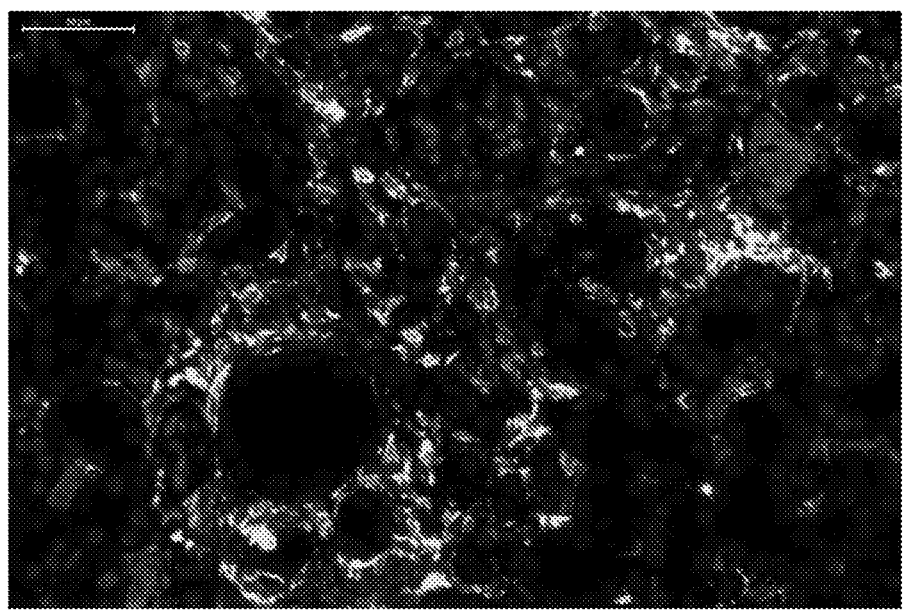
Figure 9C:
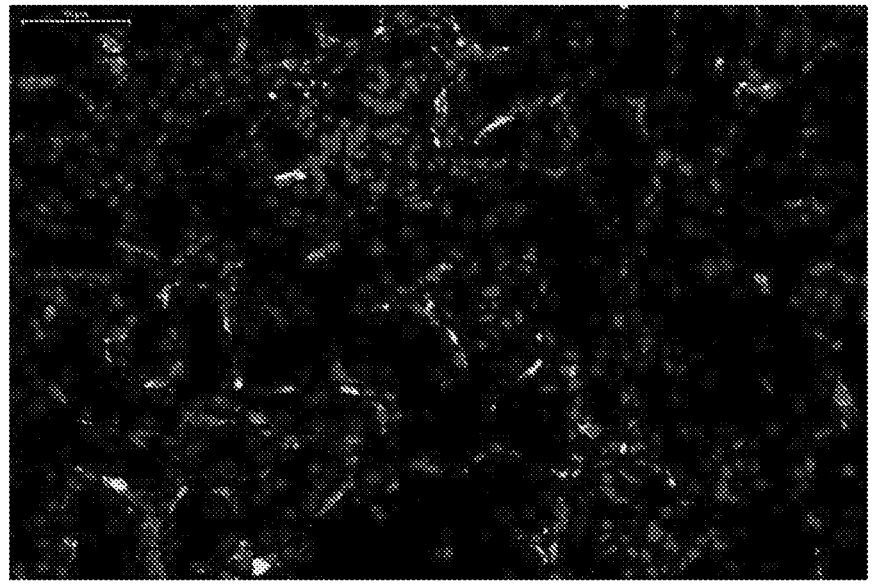
Figure 9D:
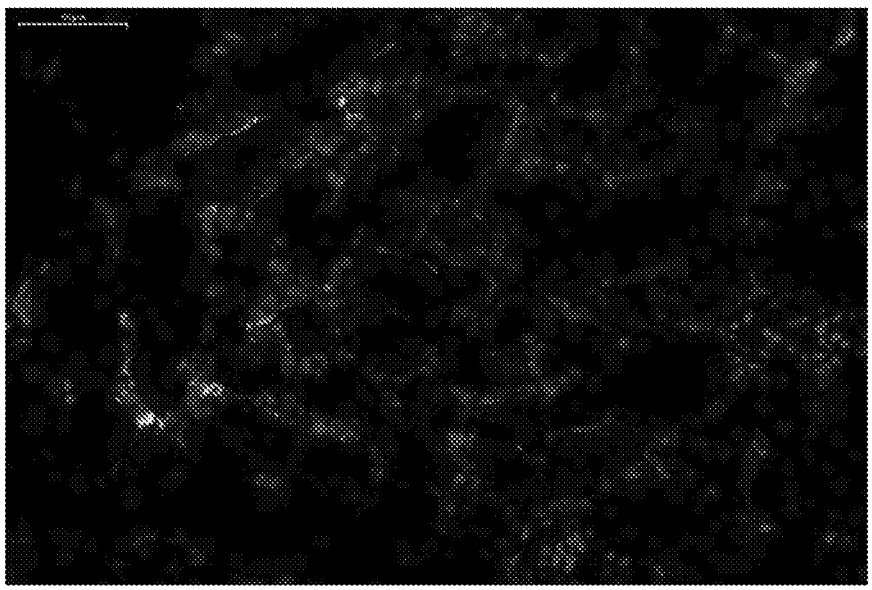
Figure 9E:

The histology of kidney samples obtained from mice treated with siNlrp3/fCNT following FA injury was assessed by Periodic acid-Schiff (PAS) staining. Unlike healthy control mouse tissue, FA only treated samples displayed significant mucopolysaccharide deposits within the interstitial fibrotic lesions (compare FIG. 6(B) with FIG. 6(A) or FIG. 6(E)). Staining in the siNlrp3/fCNT treated animals following FA injury was less intense compared to the FA only treated samples. Compare FIGS. 6(C)-6(D) with FIG. 6(B).

FA-only treated mice exhibited apoptotic spleens 1 week post-administration. In contrast, animals that received siNlrp3/fCNT following FA injury had healthy spleens.

Taken together these data demonstrate that siNlrp3/fCNT is effective in improving tissue morphology and minimizing fibrosis after FA injury. Accordingly, these results demonstrate that the pharmaceutical compositions of the present technology are useful in methods for treating and/or preventing chronic kidney disease in a subject in need thereof.

Example 4: siNlrp3/fCNT Reduces Immune Cell Infiltration in Chronic Kidney Disease Animals Lymphyocyte and macrophage infiltration of the kidney is a common feature associated with chronic kidney disease in humans. The correlation between the degree of infiltration and the severity of renal injury suggests an effector function for lymphocytes and macrophages. This Example demonstrates that siNlrp3/fCNT treatment successfully reduced immune cell infiltration in a mouse model of chronic kidney disease. Vehicle treated mice were administered a single dose of PBS and sacrificed on day 14. siNlrp3 only treated mice were administered a single dose of siNlrp3/fCNT and sacrificed on day 14. Folic acid only treated mice were administered a single dose of FA and sacrificed on day 14. FA+siNlrp3/fCNT treated mice were administered FA and one or two doses of siNlrp3/fCNT 48 hours later (mice treated with a single dose of siNlrp3/fCNT were sacrificed on day 7 and mice treated with two doses were sacrificed on day 14).

Lymphocyte infiltration of the kidneys was assessed by CD3 immunohistological staining (see FIGS. 7(A)-7(E)). A marked increase in lymphocyte infiltration was observed in the FA only treated group (FIG. 7(B)). No significant increase in CD3 staining was observed in the siNlrp3/fCNT treated animals following FA injury. Compare FIGS. 7(C)-7(D) with FIG. 7(B).

Lymphocyte infiltration of the kidneys was further tested by immunohistological staining for PD-1, a marker of co-inhibitory receptor of lymphocytes (see FIGS. 8(A)-8(E)). A significant increase was observed in PD-1 positive cell populations in the FA only treated group (FIG. 8(B)). No significant increase in PD-1 staining was observed in the siNlrp3/fCNT treated animals following FA injury. Compare FIGS. 8(C)-8(D) with FIG. 8(B).

Macrophage infiltration of the kidneys was assessed by immunohistological staining for ionized calcium-binding adapter molecule 1 (Iba1), a widely recognized 'pan-macrophage' marker (see FIGS. 9(A)-9(E)). A significant increase in Iba1 positive cell populations was observed in the FA only treated mice (FIG. 9(B)). No significant increase in Iba1 staining was observed in the siNlrp3/fCNT treated animals following FA injury. Compare FIGS. 9(C)-9(D) with FIG. 9(B).

Taken together these data demonstrate that siNlrp3/fCNT is effective in reducing the infiltration of lymphocytes and macrophages in a mouse model of chronic kidney disease. Accordingly, these results demonstrate that the pharmaceutical compositions of the present technology are useful in methods for treating and/or preventing chronic kidney disease in a subject in need thereof.

Example 5: siNlrp3/fCNT Pharmacological Intervention Decreases Expression of NLRP3 and Increases Overall Health in a Mouse Model of Chronic Kidney Disease Inflammatory response is induced in order to support damaged tissue repair processes following chronic disease progression. However inflammatory responses often contribute significantly to increased tissue damage due to fibrosis and the extent of the damage. The NLRP3 inflammasome plays an important role in activating the tissue immune response. The inflammasome is fundamentally a caspase-1-activation platform that regulates the processing and secretion of pro-IL-1β and pro-IL-18 into their respective mature and active cytokines. The expression of the inflammasome/IL-1β/IL-18 axis is recognized for its role in the progression of chronic kidney disease.

Figure 10:
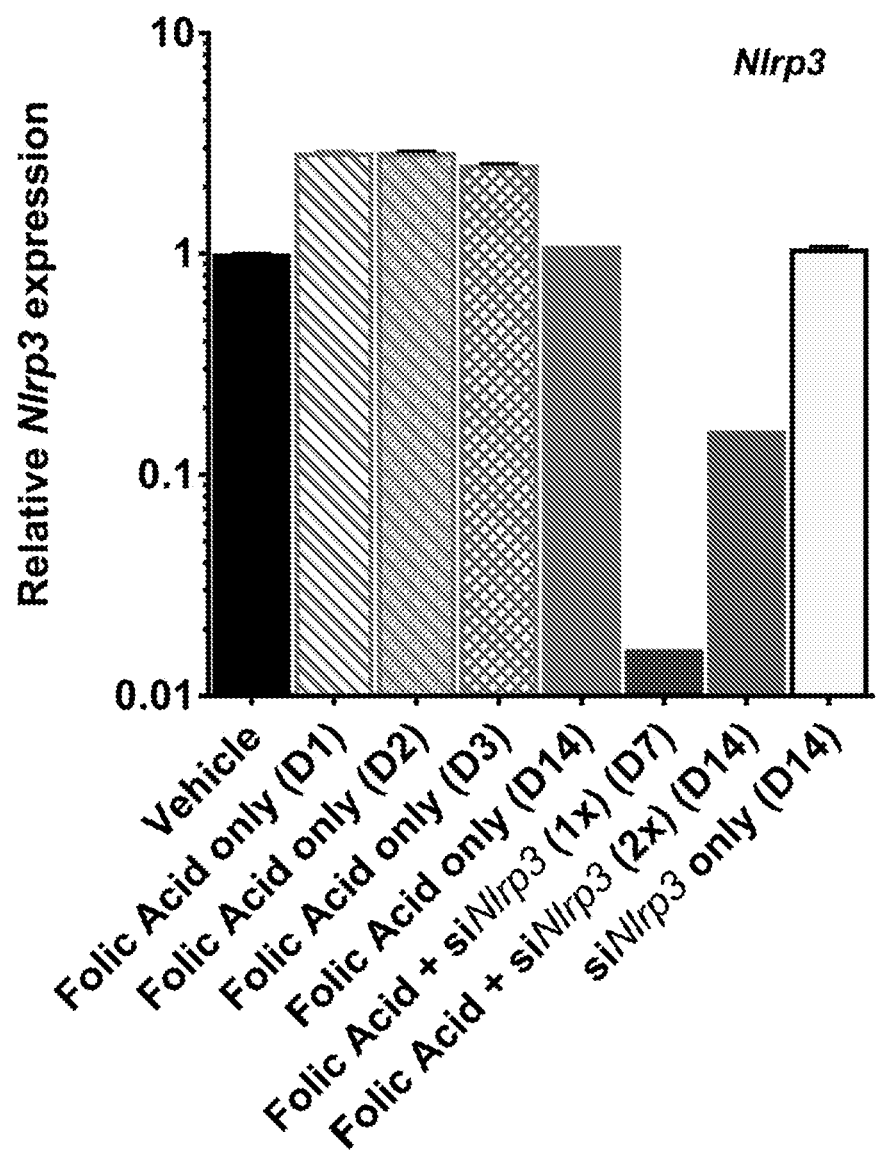
FIG. 10 shows the NLRP3 expression levels observed in various treatment groups up to 14 days post pharmacological intervention, according to the working examples, and shows siNlrp3/fCNT decreases NLRP3 expression compared to the control groups. Data are means±SEM (n=3, analyses in triplicate).

Specific NLRP3 inflammasome targeting of the siNlrp3/fCNT was confirmed by reverse transcription polymerase chain reaction (RT-PCR) of the target gene, NLRP3. Vehicle treated mice were administered a single dose of PBS and sacrificed on day 14. siNlrp3/fCNT only treated mice were administered a single dose of siNlrp3/fCNT and sacrificed on day 14. Folic acid only treated mice were administered a single dose of FA and sacrificed on days 1, 2, 3, and 14. FA+siNlrp3/fCNT treated mice were administered FA and one or two doses of siNlrp3/fCNT 48 hours later (mice treated with a single dose of siNlrp3/fCNT were sacrificed on day 7 and mice treated with two doses were sacrificed on day 14).

siNlrp3/fCNT-mediated interference was confirmed by RT-PCR. As shown in FIG. 10, a significant decrease in the expression of the NLRP3 inflammasome was observed for mice treated with FA followed by siNlrp3/fCNT intervention. A marked reduction in NLRP3 expression levels was observed in FA injured mice treated with a single dose of siNlrp3/fCNT at day 7 and after two doses of siNlrp3/fCNT at day 14.

Figure 11:
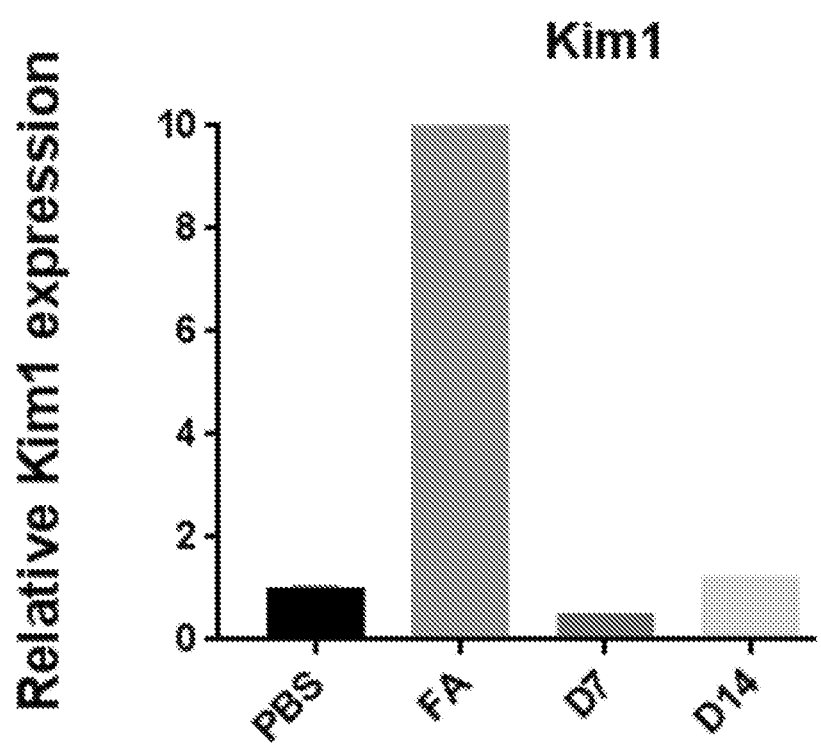
FIG. 11 illustrates siNlrp3/fCNT pharmacological intervention significantly decreases expression of Kidney Injury Molecule 1 (KIM1), according to the working examples, where KIM1 expression levels were determined by RT-PCR relative to vehicle. Data are means±SEM (n=3, analyses in triplicate).

Pharmacological knockdown of NLRP3 inflammasome expression levels with siNlrp3/fCNT had a marked effect on the expression levels of kidney injury molecule-1 (KIM1). KIM1 is a type 1 transmembrane protein that is not normally present in healthy control kidney tissue, but is highly expressed on the proximal tubule apical membrane in both the acute and chronic disease setting. As shown in FIG. 11, treatment of mice with FA only significantly increased expression levels of KIM1 in the FA only treated mice. Mice that received FA and one or two doses of siNlrp3/fCNT exhibited a significant reduction in KIM1 expression levels that resembled levels observed in healthy control mouse tissue (PBS only). See FIG. 11.

Figure 12:
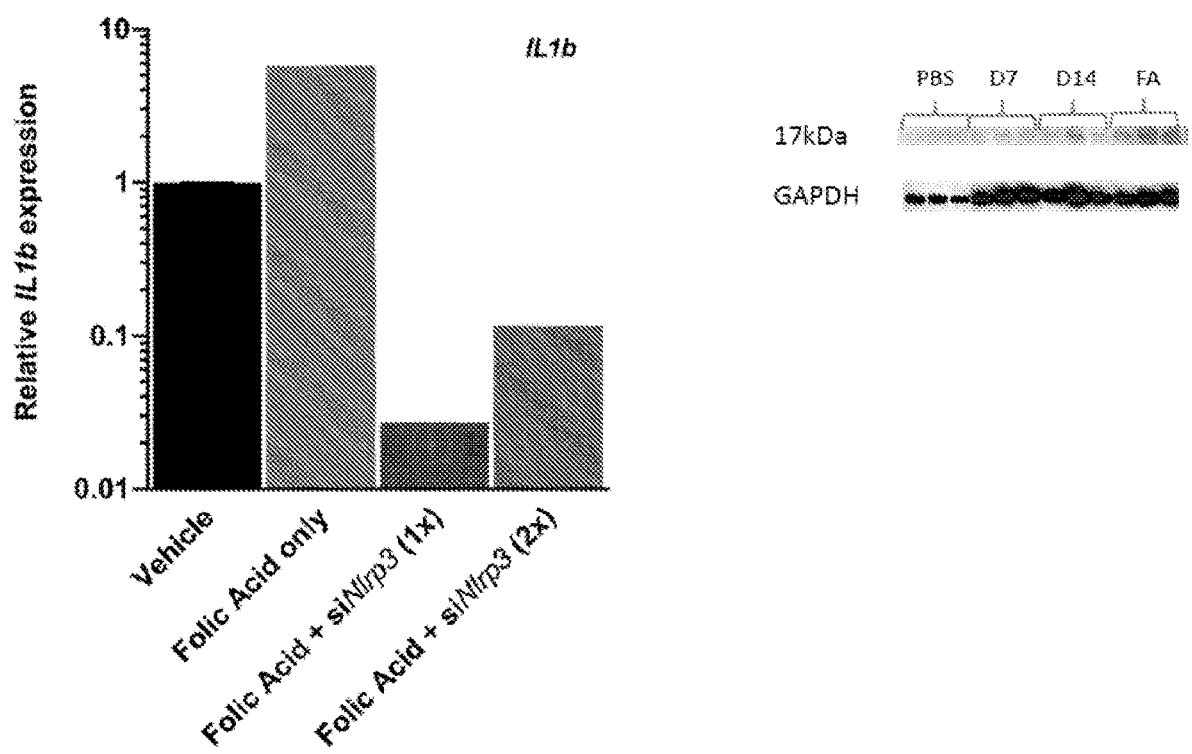
FIG. 12 illustrates siNlrp3/fCNT pharmacological intervention significantly decreases expression of IL-1β, according to the working examples, where IL-1β expression levels were determined via RT-PCR and Western blot relative to vehicle. Data are means±SEM (n=3, analyses in triplicate).
Figure 13:
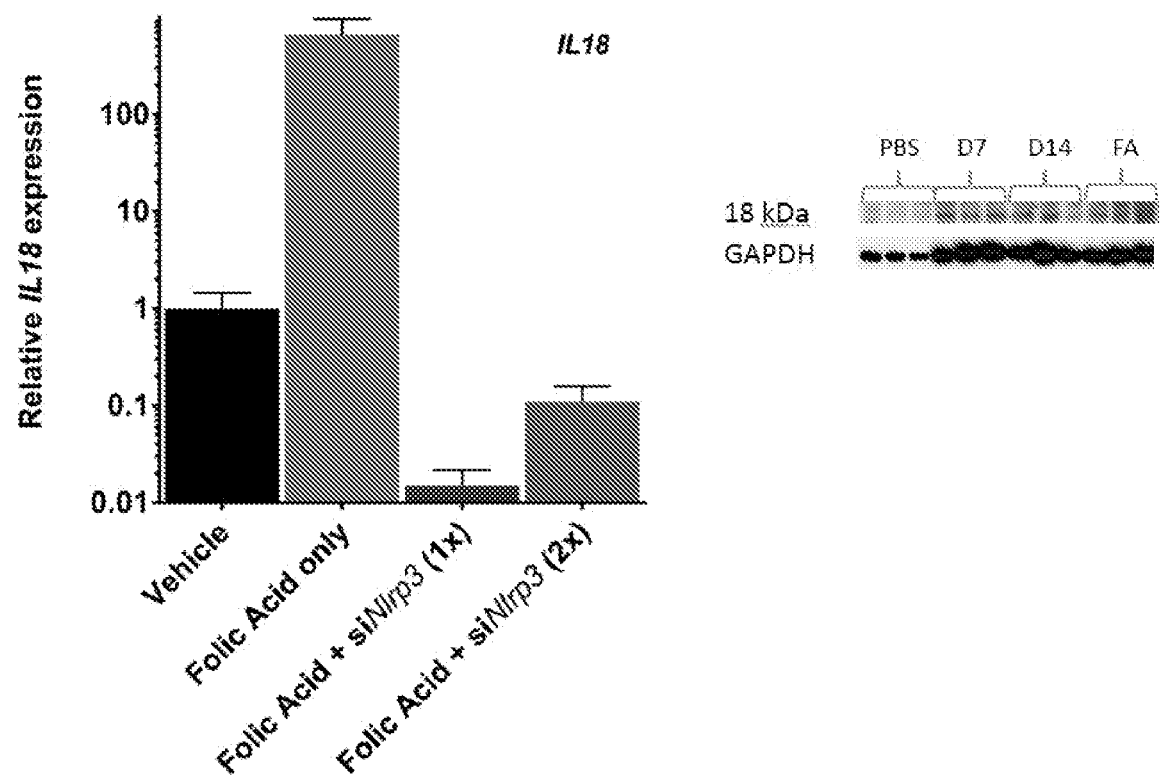
FIG. 13 illustrates siNlrp3/fCNT pharmacological intervention significantly decreases expression of IL-18, according to the working examples, where IL-18 expression levels were determined via RT-PCR and Western blot relative to vehicle. Data are means±SEM (n=3, analyses in triplicate).

Treatment of mice with FA only significantly increased expression levels of inflammatory cytokines IL-1β (FIG. 12) and IL-18 (FIG. 13). In contrast, mice that received FA and one or two doses of siNlrp3/fCNT exhibited a significant decrease in IL-1β (FIG. 12) and IL-18 (FIG. 13) levels and resembled levels observed in healthy control mouse tissue (PBS only).

Figure 14A:
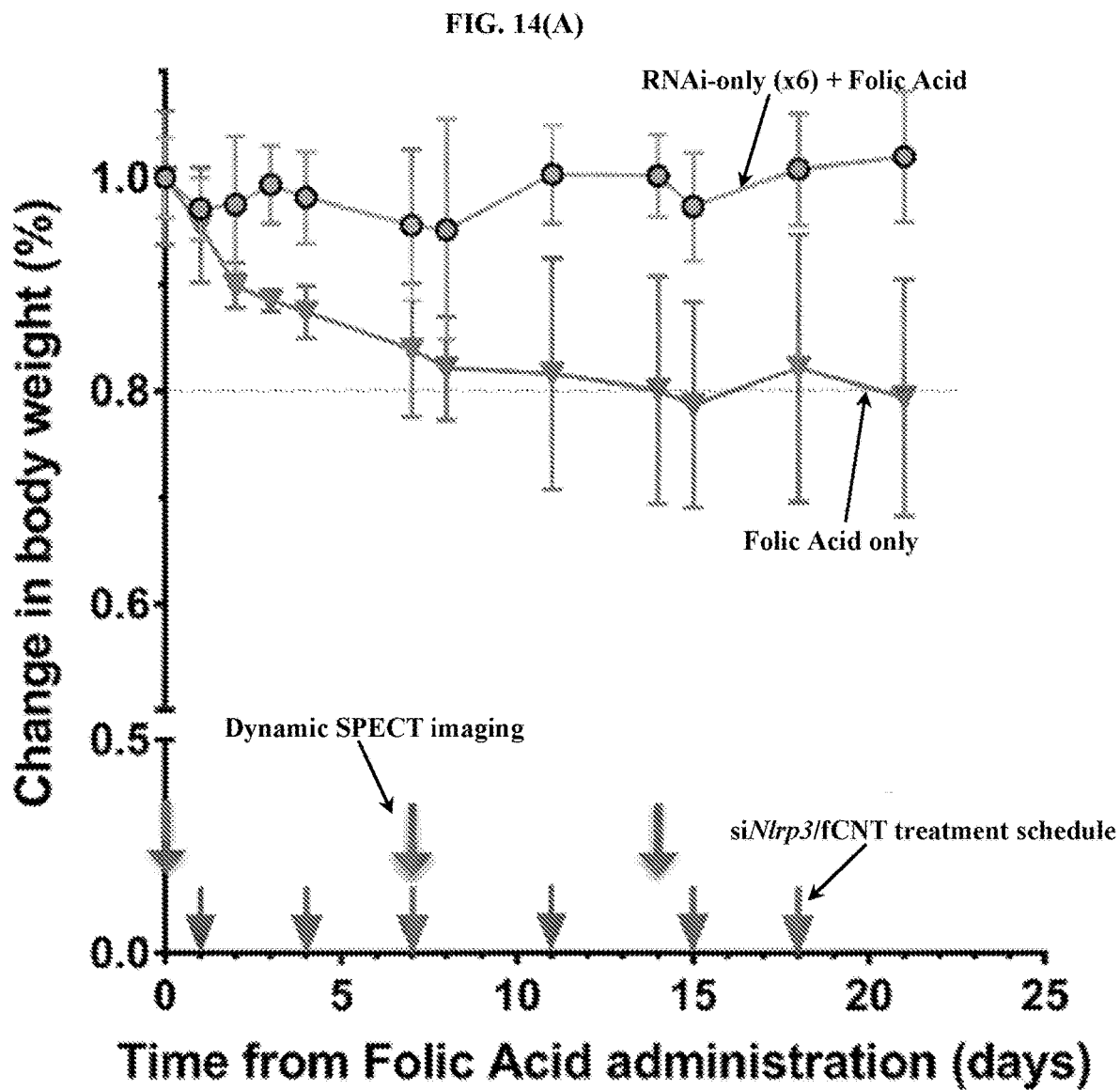
FIG. 14(A) demonstrates that siNlrp3/fCNT pharmacological intervention improves the overall health of mice in a model of chronic kidney disease. The higher (blue colored arrows) downward pointing arrows towards the X-axis indicate dynamic SPECT imaging of [$^{99m}$Tc]DTPA to measure GFR. The lower downward pointing arrows (purple) near the X-axis indicate siNlrp3/fCNT treatment schedule.
Figure 14B:
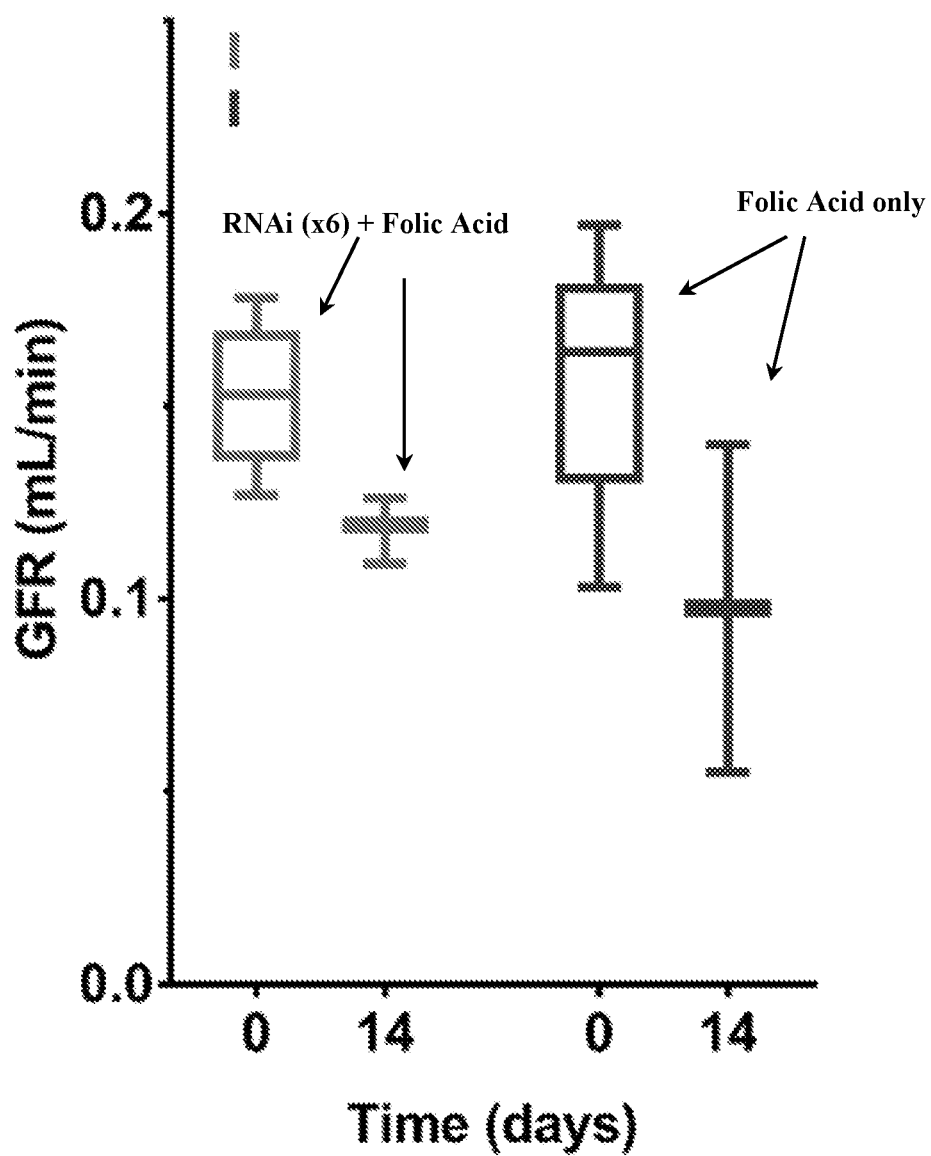
FIG. 14(B) demonstrates that siNlrp3/fCNT pharmacological intervention improves functional glomerular filtration rate (GFR) in a model of chronic kidney disease. Data are means±SEM (n=5).
Figure 15A:
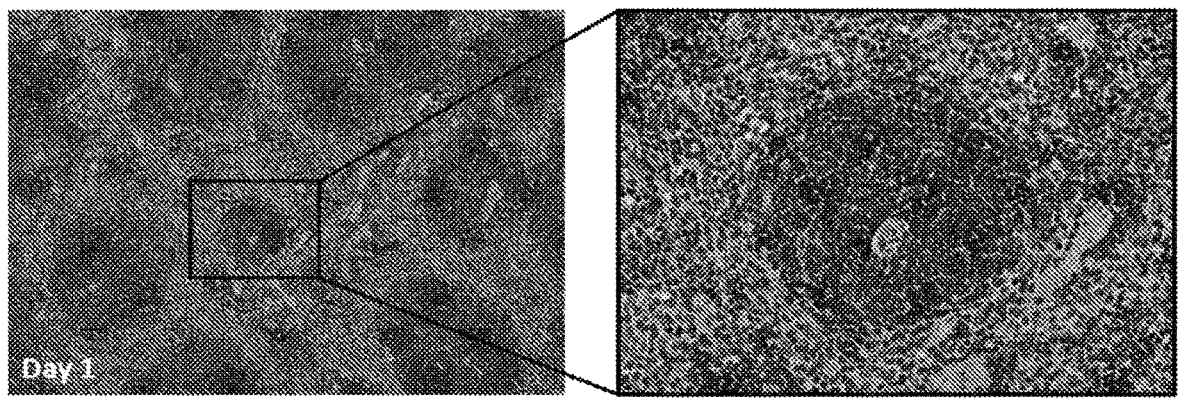
FIGS. 15(A)-15(D) provides representative images of H&E stained tissue showing the change in splenic morphology that accompanies Folic acid-induced kidney disease using only mice treated with FA (scale bars=200 µm in the left hand panels and 50 µm in right hand panels), according to the working examples, where tissue morphology was examined to assess changes after treatment with folic acid after 1 day (FIG. 15(A)), 2 days (FIG. 15(B)), 3 days (FIG. 15(C)), or 7 days (FIG. 15(D)).
Figure 15B:
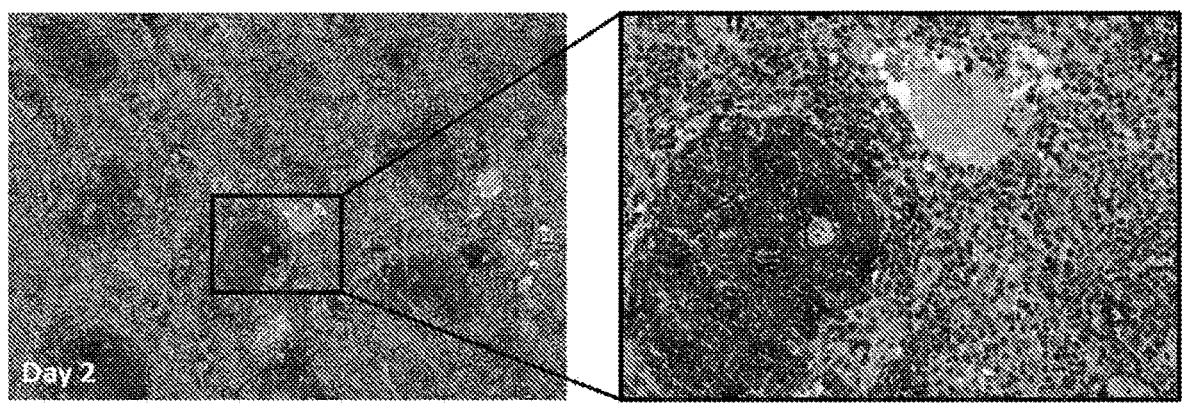
Figure 15C:
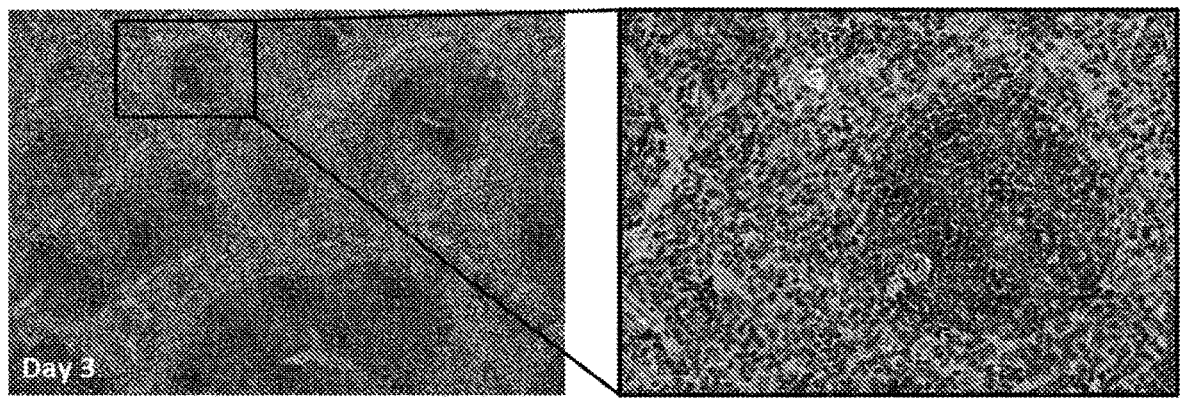
Figure 15D:
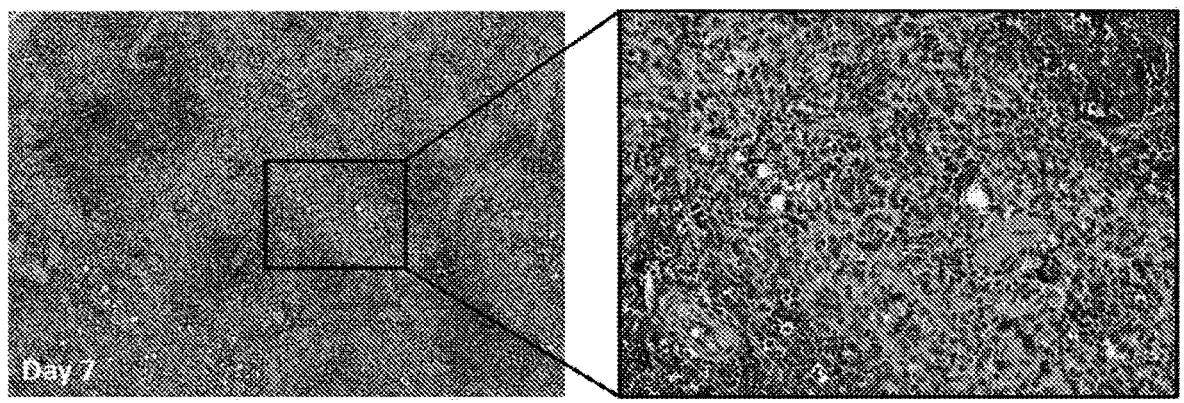

The overall health of siNlrp3/fCNT treated mice following FA injury was assessed by dynamic SPECT imaging of [$^{99m}$Tc]DTPA to measure glomerular filtration rate (GFR) of the kidneys. FIG. 14(A) demonstrates that treatment of animals with siNlrp3/fCNT following FA injury was therapeutically effective (as determined by steady body weight) and non-toxic. The untreated group with FA injury lost 20% of body mass in 2 weeks and several mice died of were euthanized for severe lethargy and morbidity. FIG. 14(B) demonstrates that siNlrp3/fCNT pharmacological intervention improves functional GFR in the mouse model of chronic kidney disease.

Accordingly, these results demonstrate that the pharmaceutical compositions of the present technology are useful in methods for treating and/or preventing chronic kidney disease in a subject in need thereof.

Example 6: siNlrp3/fCNT Improves Overall Spleen Health in Chronic Kidney Disease Animals Kidney disease can alter the homoeostasis of otherwise normal healthy tissues including spleen, liver, heart and lungs. FIGS. 15(A)-15(D) provides representative images of H&E stained tissue showing the change in splenic morphology that accompanies Folic acid-induced kidney disease using only mice treated with FA (scale bars=200 μm in the left hand panels and 50 μm in right hand panels), where tissue morphology was examined to assess changes after treatment with folic acid after 1 day (FIG. 15(A)), 2 days (FIG. 15(B)), 3 days (FIG. 15(C)), or 7 days FIG. 15(D)), and evidence the change in splenic morphology. FIGS. 17(A)-(D) show PD-1 stained splenic samples in FA only treated mice (scale bars=50 μm) after 1 day (FIG. 17(A)), 2 days (FIG. 17(B)), 3 days (FIG. 17(C)), or 7 days (FIG. 17(D)). An increase in PD-1 positive cell populations was observed to significantly increase by 7 days demonstrating injury progression.

Figure 16A:
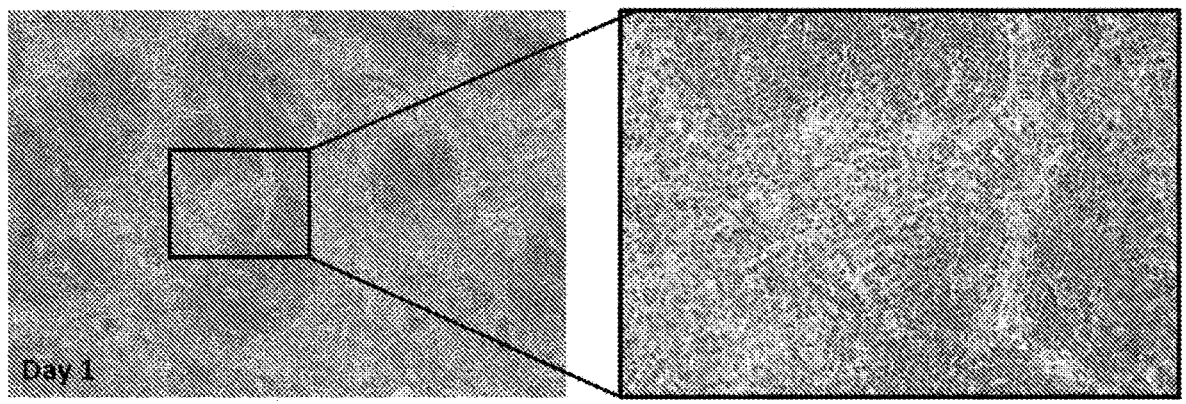
FIGS. 16(A)-16(D) show cleaved caspase 3 (CC3) stained splenic samples in FA only treated mice (scale bars=200 µm in the left hand panels and 50 µm in right hand panels), according to the working examples, after 1 day (FIG. 16(A)), 2 days (FIG. 16(B)), 3 days (FIG. 16(C)), or 7 days (FIG. 16(D))
Figure 16B:
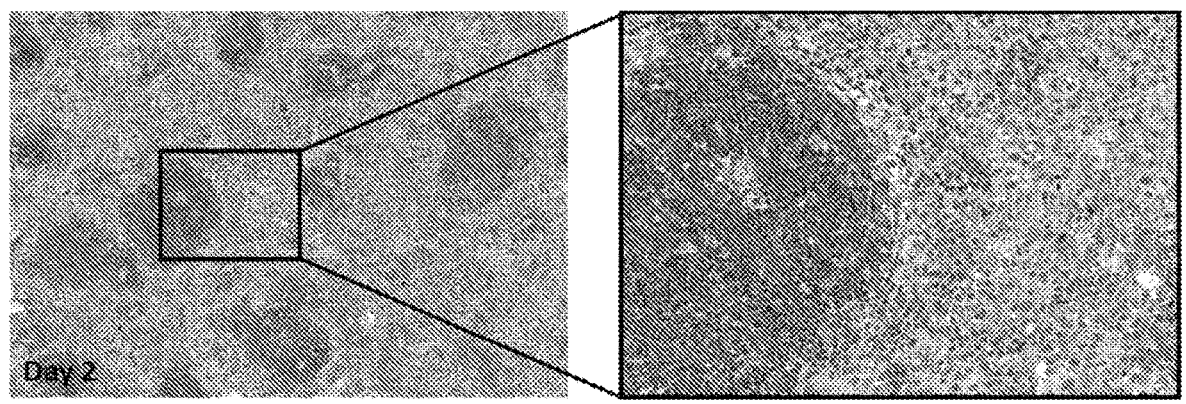
Figure 16C:
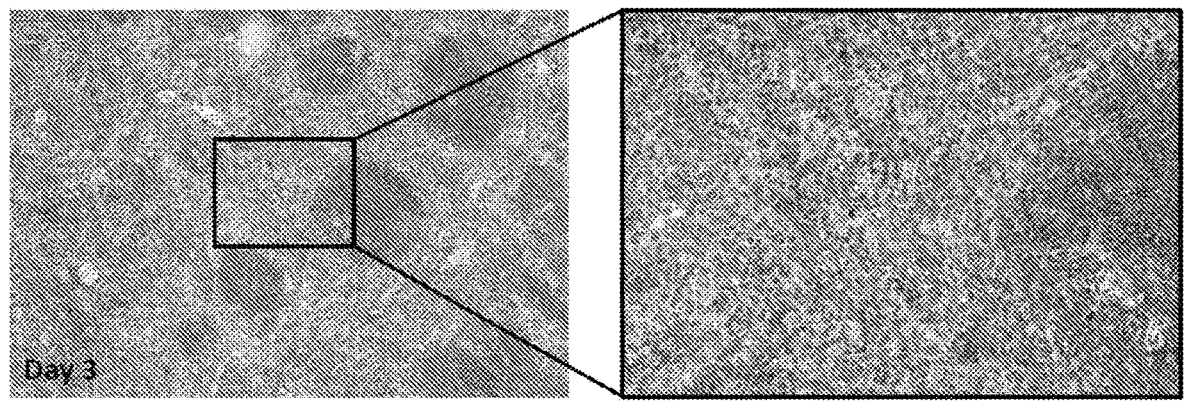
Figure 16D:
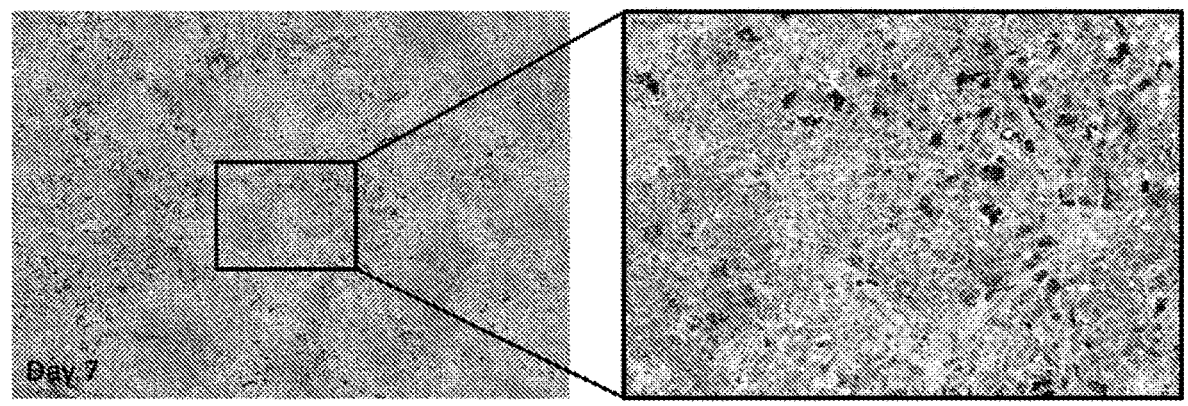
Figure 16E:
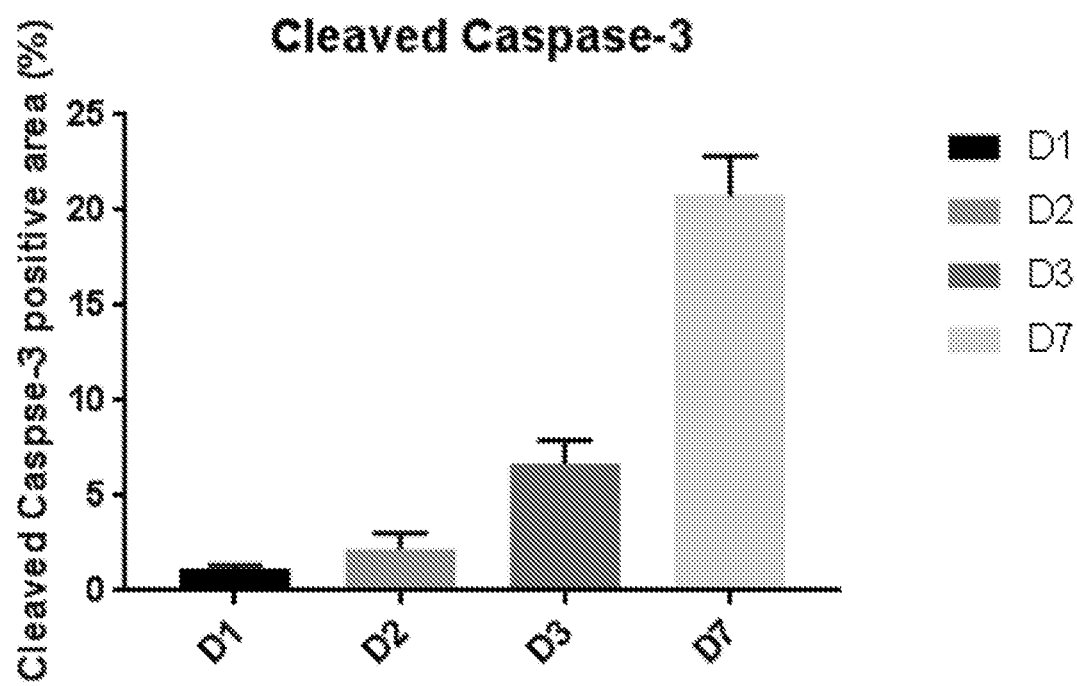
FIG. 16(E) shows scoring for CC3 positive areas in splenic samples in FA only treated mice. Unlike the spleens of these FA only treated mice, the spleens in the mice treated with siNlrp3/fCNT did not exhibit any splenic idamage, further indicating that preventing kidney damage with siNlrp3/fCNT prevented off-target secondary tissue disease.
Figure 17A:
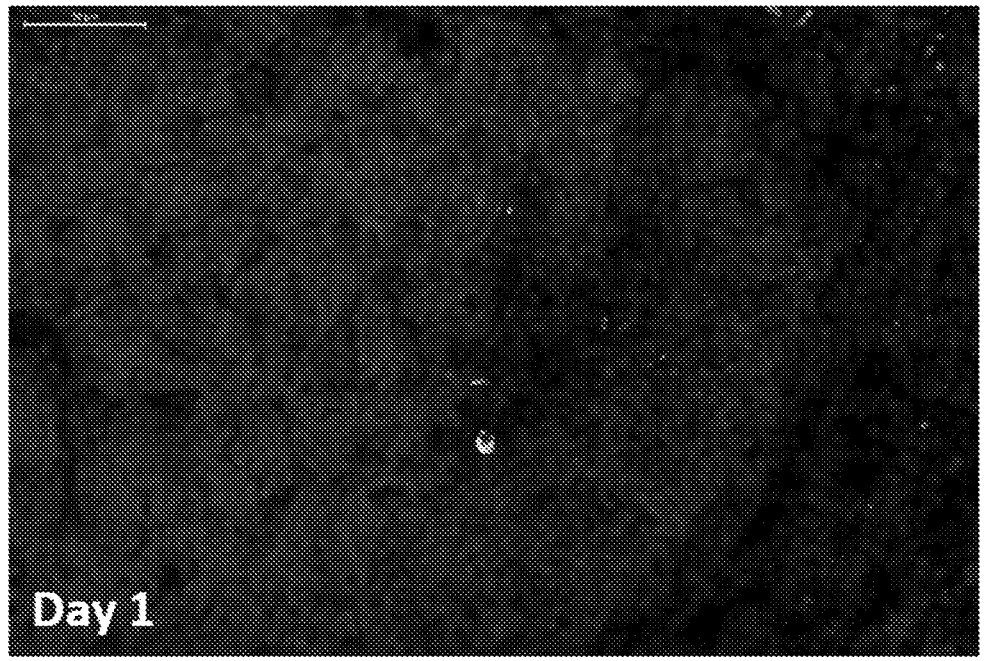
FIGS. 17(A)-(D) show PD-1 stained splenic samples in FA only treated mice (scale bars=50 µm) after 1 day (FIG. 17(A)), 2 days (FIG. 17(B)), 3 days (FIG. 17(C)), or 7 days (FIG. 17(D)). An increase in PD-1 positive cell populations was observed to significantly increase by 7 days demonstrating injury progression.
Figure 17B:
Figure 17C:
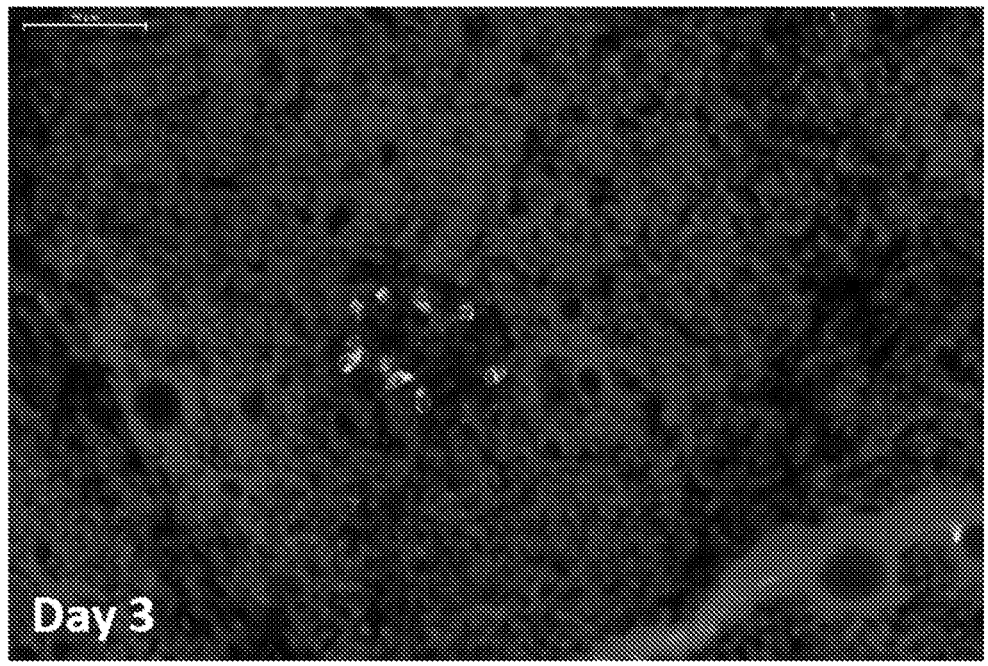
Figure 17D:
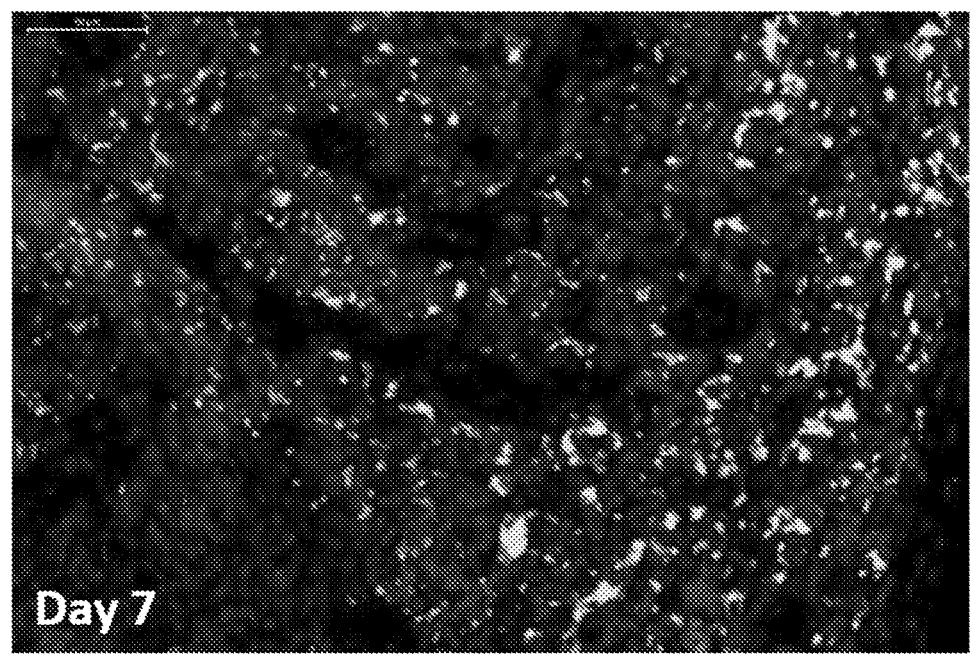

Kidney and spleen samples were stained with Cleaved caspase-3, an apoptotic marker. Activation of caspase-3 requires proteolytic processing of its inactive zymogen into activated p17 and p12 fragments. Cleavage of caspase-3 requires the aspartic acid residue at the P1 position. FIGS. 16(A)-16(D) show cleaved caspase 3 (CC3) stained splenic samples in FA only treated mice (scale bars=200 μm in the left hand panels and 50 μm in right hand panels) after 1 day (FIG. 16(A)), 2 days (FIG. 16(B)), 3 days (FIG. 16(C)), or 7 days FIG. 16(D)). Positive CC3 staining was observed primarily in red pulp, but not in white pulp. The greatest positive CC3 cells were observed in the day 7 group of spleens with 25% of the positive area. FIG. 16(E) shows scoring for CC3 positive areas in splenic samples in FA only treated mice.

Contrary to the changes illustrated in FIGS. 15(A)-15(D), FIGS. 17(A)-17(D), and FIG. 16(A)-16(E), the spleens in the mice treated with siNlrp3/fCNT did not have any splenic damage, further evidencing that preventing kidney damage with siNlrp3/fCNT prevents off-target secondary tissue disease. Thus, spenic injury and damage was ameliorated as a consequence of improving renal health according to the present technology for treating kidney disease.

EQUIVALENTS

The present technology is not to be limited in terms of the particular embodiments described in this application which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A pharmaceutical composition comprising:
a sidewall ammonium-functionalized carbon nanotube (fCNT), and
an effective amount of at least one Nlrp3 siRNA that inhibits NLR pyrin domain-containing protein 3 (NLRP3) expression levels or activity in a cell;
wherein the fCNT is non-covalently conjugated to the at least one Nlrp3 siRNA.

B. The pharmaceutical composition of Paragraph A, wherein an average molar ratio of Nlrp3 siRNA non-covalently conjugated to the fCNT in the composition is from about 1:1 to about 5:1.

C. The pharmaceutical composition of Paragraph A or Paragraph B, wherein the fCNT is a sidewall ammonium-functionalized single-wall carbon nanotube.

D. The pharmaceutical composition of Paragraph A or Paragraph B, wherein the fCNT is a sidewall ammonium-functionalized multi-wall carbon nanotube.

E. The pharmaceutical composition of any one of Paragraphs A-D, wherein primary ammonium-bearing moieties of the fCNT comprise moities represented by Formula I

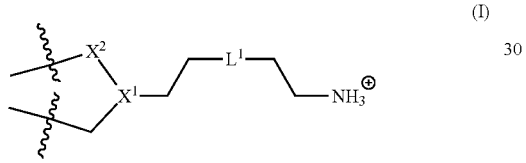

wherein
$X^1$ is O, NH, or $CH_2$;
$X^2$ is N or CH; and
$L^1$ is an alkylene glycol (such as a propylene glycol or ethylene glycol), a polyalkylene glycol (such as a poly(propylene glycol) or poly(ethylene glycol)), —NHC(O)CH($CO_2$H)—, or carbon, hydrogen, oxygen, nitrogen, sulfur, or other atom composed chain, or a combination of any two or more thereof.

F. The pharmaceutical composition of any one of Paragraphs A-E, wherein primary ammonium-bearing moieties of the fCNT comprise moities represented by Formula Ia

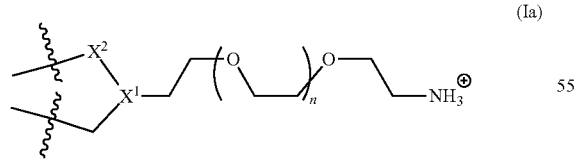

wherein
$X^1$ is O, NH, or $CH_2$;
$X^2$ is N or CH; and
n is 1, 2, 3, 4, 5, 6, 7, 8, 9, or 10.

G. The pharmaceutical composition of claim 1, wherein the at least one Nlrp3 siRNA comprises a sense strand and an antisense strand, wherein the antisense strand comprises a 20-27 base pair nucleic acid sequence that is complementary to a portion of a NLRP3 nucleic acid sequence selected from the group consisting of SEQ ID NO: 1 and SEQ ID NO: 2, optionally wherein the antisense strand comprises SEQ ID NO: 4, and optionally wherein the sense strand comprises SEQ ID NO: 3.

H. A method for treating or preventing CKD in a subject in need thereof or for treating or preventing kidney injury in a subject in need thereof, comprising administering to the subject a therapeutically effective amount of the pharmaceutical composition of any one of Paragraphs A-F.

I. The method of Paragraph H, wherein the subject displays elevated expression levels of NLRP3 protein in kidney cells prior to treatment.

J. The method of Paragraph H or Paragraph I, wherein treatment results in a decrease in NLRP3 and/or KIM1 expression levels in the subject compared to that observed in the subject prior to treatment.

K. The method of any one of Paragraphs H-J, wherein the subject has been diagnosed as having CKD.

L. The method of Paragraph K, wherein the subject exhibits signs or symptoms of CKD and wherein the signs or symptoms of CKD comprise one or more of metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis.

M. The method of any one of Paragraphs H-L, wherein the subject is human.

N. The method of any one of Paragraphs H-M, wherein the subject is a non-human mammal.

O. The method of any one of Paragraphs H-N, wherein the pharmaceutical composition is administered orally, topically, intranasally, systemically, intravenously, subcutaneously, intraperitoneally, intradermally, intraocularly, iontophoretically, transmucosally, or intramuscularly.

P. The method of any one of Paragraphs H-O, further comprising separately, sequentially or simultaneously administering one or more additional therapeutic agents to the subject.

Q. The method of Paragraph P, wherein the one or more additional therapeutic agents are selected from the group consisting of benazepril, captopril, enalapril, ramipril, lisinopril, azilsartan, candesartan, eprosartan, irbesartan, losartan, olmesartan, telmisartan, valsartan, atenolol, carvedilol, metoprolol, propranolol, amlodipine, diltiazem, felodipine, isradipine, nicardipine, nifedipine, nisoldipine, verapamil, pepstatin, CGP2928, aliskiren, chlorthalidone, chlorthiazide, hydrochlorthiazide, indapamide, metolazone, amiloride, bumetanide, furosemide, spironolactone, triamterene, and any combination thereof.

R. The method of any one of Paragraphs H-Q, wherein the pharmaceutical composition is administered daily for 6 weeks or more.

S. The method of any one of Paragraphs H-R, wherein the pharmaceutical composition is administered daily for 12 weeks or more.

T. A method for monitoring the therapeutic efficacy of the pharmaceutical composition of any one of Paragraphs A-G in a subject diagnosed with CKD or kidney injury comprising:
   (a) detecting NLRP3 protein levels in a test sample obtained from the subject after administration of the pharmaceutical composition; and
   (b) determining that the pharmaceutical composition is therapeutically effective when the NLRP3 protein levels in the test sample of step (a) are reduced compared to that observed in a control sample obtained from the subject prior to administration of the pharmaceutical composition.
U. The method of Paragraph T, further comprising detecting KIM1 levels in the subject.
V. A method for inhibiting kidney cell fibrosis and inflammation in a subject in need thereof, comprising administering to the subject a therapeutically effective amount of the pharmaceutical composition of any one of Paragraphs A-G.
W. The method of Paragraph V, wherein treatment results in the subject displaying a decrease in one or more of: collagen deposits in interstitial lesions, polysaccharides in interstitial lesions, lymphocyte infiltration into kidney cells, macrophage infiltration into kidney cells, or caspase activation.
X. A kit comprising the pharmaceutical composition of any one of Paragraphs A-G, and instructions for use.
Y. The kit of Paragraph X, wherein the instructions for use comprise instructions for a method according to any one of Paragraphs H-S.
Z. The kit of Paragraph X or Paragraph Y, wherein the instructions for use comprise instructions for a method according to Paragraph T or Paragraph U.
AA. The kit of any one of Paragraphs X-Z, wherein the instructions for use comprise instructions for a method according to Paragraph V or Paragraph W.

Other embodiments are set forth in the following claims, along with the full scope of equivalents to which such claims are entitled.

What is claimed is:

1. A pharmaceutical composition, comprising:
   a sidewall ammonium-functionalized carbon nanotube (fCNT), and
   an effective amount of at least one Nlrp3 siRNA that inhibits NLR pyrin domain-containing protein 3 (NLRP3) expression levels or activity in a cell, wherein the at least one Nlrp3 siRNA comprises a sense strand and an antisense strand, wherein the antisense strand comprises SEQ ID NO:4;
   wherein the fCNT is non-covalently conjugated to the at least one Nlrp3 siRNA.

2. The pharmaceutical composition of claim 1, wherein an average molar ratio of Nlrp3 siRNA non-covalently conjugated to the fCNT in the composition is from about 1:1 to about 5:1.

3. The pharmaceutical composition of claim 1, wherein primary ammonium-bearing moieties of the fCNT comprise moieties represented by Formula I

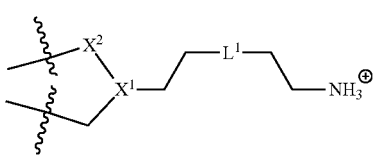

wherein
   $X^1$ is O, NH, or $CH_2$;
   $X^2$ is N or CH; and
   $L^1$ is an alkylene glycol, a polyalkylene glycol, —NHC(O)CH($CO_2$H)—, or carbon, hydrogen, oxygen, nitrogen, sulfur, or other atom composed chain, or a combination of any two or more thereof.

4. The pharmaceutical composition of claim 1, wherein the antisense strand comprises a 20-27 base pair nucleic acid sequence that is complementary to a portion of a NLRP3 nucleic acid sequence selected from the group consisting of SEQ ID NO: 1 and SEQ ID NO: 2, optionally wherein the sense strand comprises SEQ ID NO: 3.

5. A method for treating or preventing CKD in a subject in need thereof or for treating or preventing kidney injury in a subject in need thereof, comprising administering to the subject a therapeutically effective amount of the pharmaceutical composition of claim 1.

6. The method of claim 5, wherein the subject displays elevated expression levels of NLRP3 protein in kidney cells prior to treatment.

7. The method of claim 5, wherein treatment results in a decrease in NLRP3 and/or KIM1 expression levels in the subject compared to that observed in the subject prior to treatment.

8. The method of claim 5, wherein the subject has been diagnosed as having CKD.

9. The method of claim 8, wherein the subject exhibits signs or symptoms of CKD and wherein the signs or symptoms of CKD comprise one or more of metabolic acidosis, protein-energy malnutrition, loss of lean body mass, muscle weakness, peripheral edema, pulmonary edema, hypertension, anemia, fatigue, impaired cognitive function, impaired immune function, cardiovascular disease, uremia, pericarditis, encephalopathy, peripheral neuropathy, anorexia, nausea, vomiting, somnolence, erectile dysfunction, decreased libido, amenorrhea, platelet dysfunction, dry skin, pruritis, and ecchymosis.

10. The method of claim 5, wherein the subject is human.

11. The method of claim 5, wherein the subject is a non-human mammal.

12. The method of claim 5, wherein the pharmaceutical composition is administered orally, topically, intranasally, systemically, intravenously, subcutaneously, intraperitoneally, intradermally, intraocularly, iontophoretically, transmucosally, or intramuscularly.

13. The method of claim 5, further comprising separately, sequentially, or simultaneously administering one or more additional therapeutic agents to the subject.

14. The method of claim 13, wherein the one or more additional therapeutic agents are selected from the group consisting of benazepril, captopril, enalapril, ramipril, lisinopril, azilsartan, candesartan, eprosartan, irbesartan, losartan, olmesartan, telmisartan, valsartan, atenolol, carvedilol, metoprolol, propranolol, amlodipine, diltiazem, felodipine, isradipine, nicardipine, nifedipine, nisoldipine, verapamil, pepstatin, CGP2928, aliskiren, chlorthalidone, chlorthiazide, hydrochlorthiazide, indapamide, metolazone, amiloride, bumetanide, furosemide, spironolactone, triamterene, and any combination thereof.

15. The method of claim 5, wherein the pharmaceutical composition is administered daily for 6 weeks or more.

16. A method for monitoring the therapeutic efficacy of the pharmaceutical composition of claim 1 in a subject diagnosed with CKD or kidney injury comprising:
 (a) detecting NLRP3 protein levels in a test sample obtained from the subject after administration of the pharmaceutical composition; and
 (b) determining that the pharmaceutical composition is therapeutically effective when the NLRP3 protein levels in the test sample of step (a) are reduced compared to that observed in a control sample obtained from the subject prior to administration of the pharmaceutical composition.

17. The method of claim 16, further comprising detecting KIM1 levels in the subject.

18. A method for inhibiting kidney cell fibrosis and inflammation in a subject in need thereof, comprising administering to the subject a therapeutically effective amount of the pharmaceutical composition of claim 1.

19. The method of claim 18, wherein treatment results in the subject displaying a decrease in one or more of: collagen deposits in interstitial lesions, polysaccharides in interstitial lesions, lymphocyte infiltration into kidney cells, macrophage infiltration into kidney cells, or caspase activation.

20. A kit comprising the pharmaceutical composition of claim 1, and instructions for use.

21. A pharmaceutical composition, comprising:
 a sidewall ammonium-functionalized carbon nanotube (fCNT), and
 an effective amount of at least one Nlrp3 siRNA that inhibits NLR pyrin domain-containing protein 3 (NLRP3) expression levels or activity in a cell, wherein the at least one Nlrp3 siRNA comprises a sense strand and an antisense strand, wherein the sense strand comprises SEQ ID NO: 3;
 wherein the fCNT is non-covalently conjugated to the at least one Nlrp3 siRNA.

22. The pharmaceutical composition of claim 21, wherein an average molar ratio of Nlrp3 siRNA non-covalently conjugated to the fCNT in the composition is from about 1:1 to about 5:1.

23. The pharmaceutical composition of claim 21, wherein primary ammonium-bearing moieties of the fCNT comprise moieties represented by Formula I

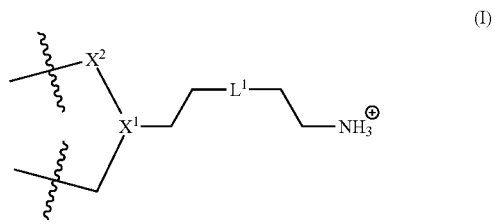

wherein
 $X^1$ is O, NH, or $CH_2$;
 $X^2$ is N or CH; and
 $L^1$ is an alkylene glycol, a polyalkylene glycol, —NHC(O)CH(CO$_2$H)—, or carbon, hydrogen, oxygen, nitrogen, sulfur, or other atom composed chain, or a combination of any two or more thereof.

24. The pharmaceutical composition of claim 21, wherein the antisense strand comprises a 20-27 base pair nucleic acid sequence that is complementary to a portion of a NLRP3 nucleic acid sequence selected from the group consisting of SEQ ID NO: 1 and SEQ ID NO: 2.

25. A kit comprising the pharmaceutical composition of claim 21, and instructions for use.

\* \* \* \* \*

SEQUENCE LISTING

<160> NUMBER OF SEQ ID NOS: 4

<210> SEQ ID NO 1
<211> LENGTH: 1756
<212> TYPE: DNA
<213> ORGANISM: Mus sp.

<400> SEQUENCE: 1

```
attactgtaa gatgtacaga cgacatgtga gaagcaggtt ctactctatc aaggacagga      60
acgcgcgtct aggtgagagt gtggacctca acagtcgcta cacgcagctc caactggtca     120
aggagcatcc aagcaagcag gagcgggagc atgaactcct gaccatcggc cggactaaaa     180
tgcgggacag ccccatgagt tcccttaagc tggagctgct gtttgagccc gaggacgggc     240
actcggagcc tgtgcacaca gtggtgttcc agggagcagc aggcatcggg aaaaccatcc     300
tagccaggaa gattatgttg gactgggcac tgggaaagct cttcaaagac aaatttgact     360
atttgttctt tatccactgc cgagaggtga gcctcaggac gccaaggagt ctagcagacc     420
tgattgtcag ctgctggcct gacccaaacc caccagtgtg caagatcctg cgcaagcctt     480
ccaggatcct cttcctcatg gatggctttg atgagctaca aggggccttt gacgagcaca     540
ttggggaggt ctgcacagac tggcaaaagg ctgtgcgggg agacattctg ctaagcagcc     600
tcatccgaaa gaaactgctg cccaaggcct ctctgctcat aacgacgagg ccggtagcct     660
tggagaaact gcagcatctc ctggaccacc cccgccatgt ggagatccta ggtttctctg     720
aggccaaaag gaaggagtat ttctttaagt atttctccaa cgagctgcag gcccgggagg     780
ccttcaggct gatccaagag aatgaggtcc tctttaccat gtgcttcatc cccctggtct     840
gctggattgt gtgcacgggg ctaaagcaac agatggagac cgggaagagc ctggcccaga     900
cctccaagac cactacggcc gtctacgtct tcttcctttc cagcctgctg caatcccggg     960
ggggcattga ggagcatctc ttctctgact acctacaggg gctctgttca ctggctgcgg    1020
atggaatttg gaaccagaaa atcctatttg aggagtgtga tctgcggaag cacggcctgc    1080
agaagactga cgtctccgct ttcctgagga tgaacgtgtt ccagaaggaa gtggactgcg    1140
agagattcta cagcttcagc cacatgactt tccaggagtt cttcgctgct atgtactatt    1200
tgctggaaga ggaggcagag gggagaccg tgaggaaagg accaggaggt tgttcagatc    1260
ttctgaaccg agacgtgaag gtcctactag aaaattacgg caagtttgaa aaaggctatc    1320
```

```
tgattttttgt tgtccgattc ctctttggcc ttgtaaacca ggagagaacc tcttatttgg    1380
agaagaaact aagttgcaag atctctcagc aagtcagact ggaactactg aagtggattg    1440
aagtgaaagc caaggccaag aagctgcagt ggcagcccag ccaactggaa ctgttctact    1500
gcctgtacga gatgcaggag gaagactttg tgcagagtgc catggaccac tttcccaaaa    1560
ttgagatcaa cctctctacc agaatggacc acgtggtttc ctccttttgt attaagaact    1620
gtcatagggt caaaacgctt tccctgggtt ttttcacaa ctcgcccaag gaggaagaag     1680
aagagaggag aggaggtcga cccttggacc aggttcagtg tgttttccca gacactcatg    1740
ttgcctgttc ttccag                                                    1756
```

<210> SEQ ID NO 2
<211> LENGTH: 1753
<212> TYPE: DNA
<213> ORGANISM: Homo sapiens

<400> SEQUENCE: 2

```
attaccgtaa gaagtacaga aagtacgtga gaagcagatt ccagtgcatt gaagacagga     60
atgcccgtct gggtgagagt gtgagcctca acaaacgcta cacacgactg cgtctcatca    120
aggagcaccg gagccagcag gagagggagc aggagcttct ggccatcggc aagaccaaga    180
cgtgtgagag ccccgtgagt cccattaaga tggagttgct gtttgacccc gatgatgagc    240
attctgagcc tgtgcacacc gtggtgttcc aggggggcggc agggattggg aaaacaatcc    300
tggccaggaa gatgatgttg gactgggcgt cggggacact ctaccaagac aggttttgact    360 atctgttcta tatccactgt cgggaggtga gccttgtgac acagaggagc ctggggggacc    420 tgatcatgag ctgctgcccc gacccaaacc cacccatcca caagatcgtg agaaaaccct    480
ccagaatcct cttcctcatg gacggcttcg atgagctgca aggtgccttt gacgagcaca    540
taggaccgct ctgcactgac tggcagaagg ccgagcgggg agacattctc ctgagcagcc    600
tcatcagaaa gaagctgctt cccgaggcct ctctgctcat caccacgaga cctgtggccc    660 tggagaaaact gcagcacttg ctggaccatc ctcggcatgt ggagatcctg ggtttctccg    720
aggccaaaag gaaagagtac ttcttcaagt acttctctga tgaggcccaa gccagggcag    780
ccttcagtct gattcaggag aacgaggtcc tcttcaccat gtgcttcatc cccctggtct    840
gctggatcgt gtgcactgga ctgaaacagc agatggagag tggcaagagc cttgcccaga    900
catccaagac caccaccgcg gtgtacgtct tcttcctttc cagtttgctg cagccccggg    960
gagggagcca ggagcacggc ctctgcgccc acctctgggg gctctgctct ttggctgcag   1020
atggaatctg gaaccagaaa atcctgtttg aggagtccga cctcaggaat catggactgc   1080
agaaggcgga tgtgtctgct ttcctgagga tgaacctgtt ccaaaaggaa gtggactgcg   1140
agaagttcta cagcttcatc cacatgactt tccaggagtt ctttgccgcc atgtactacc   1200
tgctggaaga ggaaaaggaa ggaaggacga acgttccagg gagtcgtttg aagcttccca   1260
gccgagacgt gacagtcctt ctggaaaact atggcaaatt cgaaagggg tatttgattt    1320 ttgttgtacg tttcctcttt ggcctggtaa accaggagag gacctcctac ttggagaaga   1380
aattaagttg caagatctct cagcaaatca ggctggagct gctgaaatgg attgaagtga   1440
aagccaaagc taaaaagctg cagatccagc ccagccagct ggaattgttc tactgtttgt   1500
acgagatgca ggaggaggac ttcgtgcaaa gggccatgga ctattccccc aagattgaga   1560
tcaatctctc caccagaatg gaccacatgg tttcttcctt ttgcattgag aactgtcatc   1620
```

```
-continued gggtggagtc actgtccctg gggtttctcc ataacatgcc caaggaggaa gaggaggagg    1680
aaaaggaagg ccgacacctt gatatggtgc agtgtgtcct cccaagctcc tctcatgctg    1740
cctgttctca tgg                                                       1753

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
cuuucccaaa auugagauca acctc                                            25

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gagguugauc ucaauuuugg gaaagug                                          27
```